(12) United States Patent
Yang et al.

(10) Patent No.: US 10,206,920 B2
(45) Date of Patent: Feb. 19, 2019

(54) PHARMACEUTICAL COMPOSITION FOR TREATING CANCER AND A METHOD OF USING THE SAME

(71) Applicant: SUZHOU INSTITUTE OF SYSTEMS MEDICINE, Suzhou (CN)

(72) Inventors: Yili Yang, Suzhou (CN); Long Cui, Suzhou (CN); Tingyu Wu, Suzhou (CN)

(73) Assignee: SUZHOU INSTITUTE OF SYSTEMS MEDICINE, Suzhou (CN)

( * ) Notice: Subject to any disclaimer, the term of this patent is extended or adjusted under 35 U.S.C. 154(b) by 19 days.

(21) Appl. No.: 15/812,557

(22) Filed: Nov. 14, 2017

(65) Prior Publication Data
US 2018/0133214 A1  May 17, 2018

Related U.S. Application Data

(60) Provisional application No. 62/422,598, filed on Nov. 16, 2016.

(51) Int. Cl.
*A61K 31/497* (2006.01)
(52) U.S. Cl.
CPC ........ *A61K 31/497* (2013.01); *A61K 2300/00* (2013.01)
(58) Field of Classification Search
CPC .................................................. A61K 31/497
See application file for complete search history.

(56) References Cited

PUBLICATIONS

Lenz, HJ, Clinical update: proteasome inhibitors in solid tumors, 2003, Cancer Treatment Reviews, 23, Suppl. I, pp. 41-48 (Year: 2003).*
Gravina et al., Nucleo-cytoplasmic transport as a therapeutic target of cancer, 2014, Journal of Hematology & Oncology, 7:85, pp. 1-9 (Year: 2014).*
Turner et al., Inhibition of CRM1-dependent nuclear export sensitizes malignant cells to cytotoxic and targeted agents, 2014, Seminars in Cancer Biology, 27, pp. 62-73 (Year: 2014).*
Tingyu Wu et al., "Nuclear Export of Ubiquitinated Proteins Determines the Sensitivity of Colorectal Cancer to Proteasome Inhibitor," Mol Cancer Ther; 2017, pp. 1-12.

* cited by examiner

*Primary Examiner* — Jeffrey S Lundgren
*Assistant Examiner* — Tori Strong
(74) *Attorney, Agent, or Firm* — SZDC Law P.C.

(57) ABSTRACT

The invention provides a pharmaceutical composition and a method for treating cancer, and the composition comprises a proteasome inhibitor and a nuclear export inhibitor. The composition has synergistic effects on treating cancers, particularly a solid tumor cancer. Specifically, the proteasome inhibitor bortezomib and CRM1 inhibitor KPT330 induce apoptosis and cell cycle arrest in sensitive cells, such as HCT116 and RKO cells. Bortezomib induces the nuclear export of p53, whereas it could be effectively blocked by KPT330. CRM1 inhibitor KPT330 synergistically sensitizes CRC cells to bortezomib treatment in vitro and in vivo, through inhibiting nuclear export and restoring functions of p53. The invention also provides use of proteasome inhibitor in a solid tumor cancer. The invention provides a rationale for the use of proteasome inhibitor together with nuclear export blocker in the treatment of cancers, such as colorectal cancer.

10 Claims, 25 Drawing Sheets

| Cell line | Bortezomib (nM) | KPT330(nM) | |
|---|---|---|---|
| | | 10 | 100 |
| HCT116 | 1 | 0.23 | 0.54 |
| | 5 | 0.47 | 0.69 |
| | 10 | 0.60 | 0.77 |
| RKO | 2 | 0.11 | 0.61 |
| | 10 | 0.59 | 0.69 |
| | 50 | 0.64 | 0.75 |
Combination Index
Fig. 2D
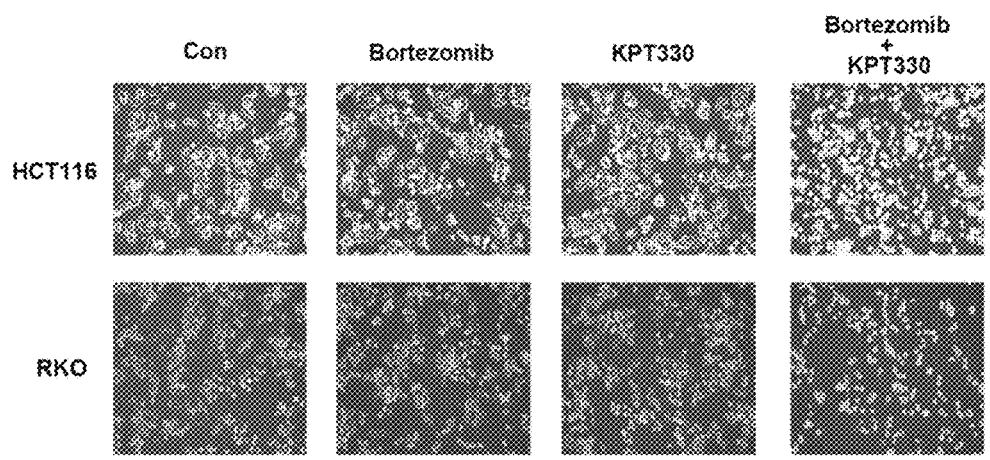
Fig. 2E
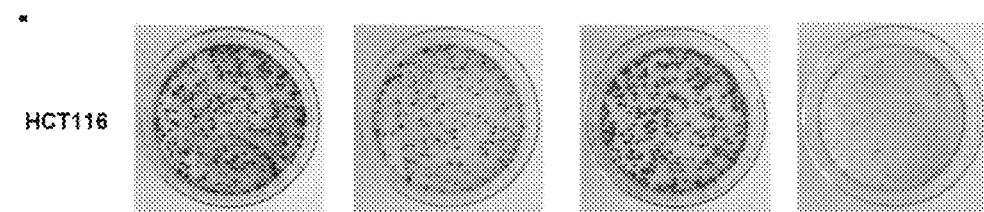
Fig. 2F

| Number | Gender | Age | Tumor | Type | TNM Staging | Differentiation | FOLFOX treatment |
|---|---|---|---|---|---|---|---|
| CRC0008 | male | 73 | rectum | adenoma | T4N2M0 | II | resistance |
| CRC3496 | male | 65 | colon | adenoma | T3N1M1 | II-III | resistance |
| CRC3547 | male | 72 | rectum | mucinous adenoma | T3N1M1 | III | resistance |
| CRC3405 | female | 57 | colon | adenoma | T4N1M1 | II-III | resistance |
| CRC6227 | female | 61 | rectum | adenoma | T3N1M0 | II-III | resistance |
| CRC3612 | female | 68 | rectum | adenoma | T3N0M1 | II-III | resistance |

PHARMACEUTICAL COMPOSITION FOR TREATING CANCER AND A METHOD OF USING THE SAME

CROSS REFERENCE TO RELATED APPLICATIONS

This application claims priority to U.S. Provisional Application Ser. No. 62/422,598 filed Nov. 16, 2016, entitled "Inhibition of nuclear export as a means to enhance chemotherapeutics that activate tumor suppressor p53", which is incorporated herein by reference in its entirety and for all purposes.

FIELD OF THE INVENTION

The present invention relates to the field of pharmaceuticals for cancers, and more particularly to a pharmaceutical composition and a method for treating cancer, as well as use of a proteasome inhibitor in a solid tumor cancer.

DESCRIPTION OF THE RELATED ART

Although proteasome inhibitors such as bortezomib had significant therapeutic effects in multiple myeloma and mantel cell lymphoma, they exhibited minimal clinical activity as a mono-therapy for solid tumors, including colorectal cancer.

Colorectal cancer (CRC) is one of the most common malignancies with estimated more than 1.2 million new cases each year worldwide. Noteworthily, its incidence rate has been increasing in many developing areas over the last several decades despite the downward trend in developed countries. As the majority of patients are diagnosed at advanced stages, and the relapse of the tumor that has become resistance to the 5-fluorouracil- and oxaliplatin-based combination chemotherapy, the 5-year survival rate for patients with CRC remains quite low. Thus, early diagnosis through targeted screening and finding new targets and approaches for the treatment are sorely needed to improve the prognosis of individuals with CRC.

It has been shown that alterations of the ubiquitin-proteasome system are critical for cancer initiation and development, often through enhanced degradation of tumor suppressors and reduced degradation of oncoproteins. Genomic analyses also revealed that mutations of ubiquitination-related proteins, including APC, p53, Fbw7 and Smad4, are the characteristic changes of CRC. Proteasome inhibitors such as bortezomib are able to induce growth arrest and apoptosis in CRC cells in vitro. Bortezomib has also been approved for the treatment of multiple myeloma and mantle cell lymphoma. However, bortezomib or newer generation of proteasome inhibitors had minimal anti-tumor activity in patients with advanced CRC or other solid tumors. These results prompted significant efforts to combine proteasome inhibitors with other anti-tumor strategies, including conventional chemotherapy, radiation and other targeted therapy. At present, the promise of proteasome inhibitors in the treatment of solid tumors has yet to be realized.

Precisely controlled transportation of protein across nuclear membrane is critical for proper growth, death and differentiation of eukaryotic cells. It has been shown that chromosome region maintenance 1 (CRM-1) recognizes nuclear export signal (NES) of target proteins and mediates the nuclear export of many tumor suppressorproteins (TSP), such as p53, FOXO, RB1, and CDKN1A. CRM-1 is upregulated in a variety of cancers, and responsible for aberrant cytoplasmic localization and inactivation of tumor suppressors. Furthermore, specific CRM-1 inhibitor KPT330 (Selinexor) has broad anti-tumor activity in various tumors and is being actively explored as a novel cancer therapeutic agent. FDA has designated Selinexor orphan drug status for certain types of leukemia and lymphoma.

SUMMARY OF THE INVENTION

To solve the above technical problems, the present invention provides a pharmaceutical composition for treating cancer, and the pharmaceutical composition has synergistic effects on inducing apoptosis of cancer cells, thereby achieving excellent therapeutic effects on various cancers, particularly the solid tumor cancers containing wild type p53. The invention also provides a method for treating a cancer, as well as a method for treating a solid tumor cancer.

To achieve the above purposes, the present invention utilizes the following technical solutions.

In one aspect, the invention provides a pharmaceutical composition for treating cancer, the pharmaceutical composition comprises:

a proteasome inhibitor or a pharmaceutically acceptable salt, solvate, hydrate, cocrystal or prodrug thereof; and a nuclear export inhibit or a pharmaceutically acceptable salt, solvate, hydrate, cocrystal or prodrug thereof.

Preferably, the proteasome inhibitor is bortezomib or corfilzomib.

Preferably, the nuclear export inhibitor is a CRM1 inhibitor.

More preferably, the CRM1 inhibitor is selected from the group consisting of KPT330, KPT-8602, KPT-185, KPT-276 and KPT-335.

Preferably, the pharmaceutical composition has synergistic effects on inducing apoptosis of cancer cells.

Preferably, the pharmaceutical composition exhibits synergistic cytotoxicity on cancer cells.

In a preferable embodiment, the pharmaceutical composition comprises bortezomib and KPT330.

In a more preferable embodiment, the cancer is a solid tumor cancer, and the cancer cells contain wild type p53.

In a more still preferable embodiment, the solid tumor cancer is a colorectal cancer, and the cancer cells are HCT116 or RKO cells with wild type p53.

There is a synergistic effect between bortezomib and KPT330 in HCT116 (p53 wild type) and RKO (p53 wild type) cells, and combination of bortezomib and KPT330 has significantly increased inhibition on colony formation on HCT116 cells than either drug alone. It is suggested that the synergistic effects depend on the function of p53.

Preferably, the composition also comprises a biocompatible excipient.

In another aspect, the invention also provides a method for treating cancer, comprising administrating to a subject in need thereof a therapeutically effective amount of composition comprising a proteasome inhibitor or a pharmaceutically acceptable salt, solvate, hydrate, cocrystal or prodrug thereof and a nuclear export inhibitor or a pharmaceutically acceptable salt, solvate, hydrate, cocrystal or prodrug thereof, as an active agent.

Preferably, the proteasome inhibitor is bortezomib or corfilzomib.

Preferably, the nuclear export inhibitor is a CRM1 inhibitor, and the CRM1 inhibitor is selected from the group consisting of KPT330, KPT-8602, KPT-185, KPT-276 and KPT-335.

More preferably, the subject has cancer cells containing wild type p53.

Still more preferably, the cancer is a solid tumor cancer selected from the group consisting of colorectal cancer, gastric cancer, ovarian cancer, and head and neck cancer.

Preferably, the pharmaceutical composition is administrated to the subject intramuscularly, orally or intravenously to result in an effective dosing regimen.

Preferably, the pharmaceutical composition is administered to the subject at least three times a week.

Specifically, the subject is a human.

In still another aspect, the invention further provides a method for treating a solid tumor cancer, comprising simultaneously administering to a subject with a proteasome inhibitor and a nuclear export inhibitor.

Preferably, the proteasome inhibitor is bortezomib or corfilzomib.

Preferably, the nuclear export inhibitor is a CRM1 inhibitor, and the CRM1 inhibitor is selected from the group consisting of KPT330, KPT-8602, KPT-185, KPT-276 and KPT-335.

Preferably, the subject has cancer cells containing wild type p53.

Preferably, the solid tumor cancer is selected from the group consisting of colorectal cancer, gastric cancer, ovarian cancer, and head and neck cancer.

Preferably, the proteasome inhibitor and the nuclear export inhibitor are administered to the subject intramuscularly, orally or intravenously.

Preferably, the proteasome inhibitor and the nuclear export inhibitor are administered to the subject at least three times a week.

In the present study, we found that exposing CRC cells to proteasome inhibitors induced nuclear export of ubiquitinated proteins, and hypothesized that such export represents a cellular protective mechanism that reduces the anti-tumor effect of proteasome inhibition. When treating CRC cells with bortezomib in the presence of KPT330, they synergistically induced apoptosis and G2/M cell cycle block in p53+/+ cells, which was accompanied by increase of nuclear p53. The synergistic action could be mimicked by CRM1 knockdown and largely abolished by knocking down p53. Furthermore, bortezomib and KPT330 had synergistic action against HCT116 xenografts and primary tumor-derived xenografts possessing functional p53. These results indicate inhibition of nuclear export sensitizes CRC to proteasome inhibitor-induced p53-dependent apoptosis and cell cycle block, and provide a rationale for the combination therapy using inhibitors for proteasome and nuclear export.

We found in the present study that proteasome inhibition induced a remarkable nuclear exportation of ubiquitinated proteins. Inhibition of CRM1, the nuclear export carrier protein, hampered protein export and synergistically enhanced the cytotoxic action of bortezomib on colon cancer cells containing wild type p53, which underwent G2/M cell cycle block and apoptosis. Further analysis indicated that tumor suppressor p53 was one of the proteins exported from nuclei upon proteasome inhibition, and in the presence of CRM1 inhibitor KPT330, nuclear p53 and expression of its target genes were increased markedly. Moreover, knockdown of p53 with a specific siRNA significantly reduced the synergistic cytotoxic action of bortezomib and KPT330 on p53+/+ HCT116 cells. In mice, KPT330 markedly augmented the anti-tumor action of bortezomib against HCT116 xenografts as well as primary tumor-derived xenografts that harbored functional p53. These results indicate that nuclear p53 is a major mediator in the synergistic anti-tumor effect of bortezomib and KPT330, and provides a rationale for the use of proteasome inhibitor together with nuclear export blocker in the treatment of colorectal cancer. It is conceivable that targeting nuclear exportation may serve as a novel strategy to overcome resistance and raise chemotherapeutic efficacy, especially for the drugs that activate the p53 system.

As compared with the prior art, the invention has the following advantages: the pharmaceutical composition of the invention comprises a proteasome inhibitor and a CRM inhibitor, and has synergistic effects on treating cancers, particularly a solid tumor cancer, and the synergistic effects depend on the function of p53. Bortezomib and KPT330 induce apoptosis and cell cycle arrest in sensitive cells, such as HCT116 and RKO cells. And the co-treatment of bortezomib and KPT330 inhibit HCT116 xenografts. Nuclear p53 plays a critical role in synergistic cytotoxic effects, bortezomib induces the nuclear export of p53, whereas it could be effectively blocked by KPT330. CRM1 inhibitor KPT330 synergistically sensitizes CRC cells to bortezomib treatment in vitro and in vivo, through inhibiting nuclear export and restoring functions of p53.

BRIEF DESCRIPTION OF THE DRAWINGS

In order to illustrate the technical solutions in the embodiments of the present invention more clearly, the accompanying drawings used in the embodiments will be described simply. Obviously, the accompanying drawings described hereinafter only are some embodiments of the present invention, and other drawings also can be obtained without creative work for those skilled in the art.

(FIG. 1B) HeLa cells were treated with MG132 (30 μM) and LMB (20 nM) for 12 h as indicated followed by fractionation into nuclear (N) and cytoplasmic (FIG. 1C) fractions. Equal amount of proteins from these fractions were processed for immunoblotting with an anti-ubiquitin antibody. Tubulin and Histone H3 were detected as markers for cytoplasmic and nuclear fractions, respectively. (FIGS. 1C, 1D) HCT116 and RKO cells were treated with bortezomib (5 nM) and KPT330 (100 nM) for 12 h as indicated. The cells were fixed and stained for ubiquitin-conjugated proteins (FK2). Bars represent 10 μm.

FIGS. 2A-2H that bortezomib and KPT330 exhibit synergistic cytotoxicity in HCT116 and RKO cells. (FIG. 2A) SW480, SW620, HCT116 and RKO cells were cultured in 96-well plates and incubated with the different doses of bortezomib or KPT330 for 72 h. Effects on proliferation were assayed by CCK8 experiment. $IC_{50}$ of both drugs were calculated. (FIG. 2B, FIG. 2C) Colorectal cancer cells were treated with bortezomib and KPT330 at the indicated concentrations for 72 h. Cell viability was measured by CCK8. (FIG. 2D) The synergistic cytotoxicity was quantitatively analyzed by Combination Index (CI) in HCT116 and RKO cells using the Calcusyn software program. CI=1 indicates additivity, CI>1 indicates antagonism, and CI<1 indicates synergism. (FIG. 2E) Cellular morphology alteration in response to drug treatment for 72 h was observed with inverted microscope. (FIG. 2F) Clone formation assay of HCT116 with treatment of bortezomib or KPT330 alone or combination. (FIG. 2G) The knockdown efficiency of siRNA of CRM1 was confirmed by real-time PCR analysis. (FIG. 2H) After knocking down the expression of CRM1, HCT116 cells were treated with or without bortezomib (5 nM) for 72 h. CCK8 assay was performed to detect cell viability in different groups. The bars represent the mean±SEM of triplicates in one experiment.

(FIG. 3A) HCT116 and RKO cells were treated with bortezomib, KPT330 or their combination for 48 h at the indicated concentrations. The cells were subsequently stained with annexin V, apoptotic cells were distinguished by flow cytometric analysis. (FIG. 3B) Measurement of caspase-3 and -7 by means of a luminometric assay was performed in cells receiving the same treatment. (FIG. 3C) HCT116 was treated for 48 h with 5 nM bortezomib in combination with 100 nM KPT330 in the presence of 4 µM pancaspase inhibitor Z-VAD-FMK, stained with annexin V, and analysed by flow cytometry. (FIG. 3D) The 48 h treatment with the combination of bortezomib and KPT330 increased expression of cleaved PARP1. (FIG. 3E, FIG. 3F) HCT116 and RKO cells were treated with bortezomib (5 nM), KPT330 (100 nM) or their combination for 48 h. Cells were fixed and stained with PI followed by flow cytometric analysis for DNA content. A representative DNA histogram is shown for each condition. The bars represent the mean±SEM of triplicates in one experiment.

(FIG. 4A) Relative tumor growth of HCT116 xenografts treated with vehicle (control), 1 mg kg/ml of bortezomib, 10 mg/kg of KPT330 or in combination measured from 0 to 18 days post treatment. (n=10). (FIG. 4B) Immunohistochemical staining of p53, Ki67 and DNA fragmentation in tumor tissues. (FIG. 4C) Quantitative statistics of the Immunohistochemical staining. Bars represent 100 µm. The data shown represent the mean±SEM.

(FIG. 5A) Immunofluorescence with p53 antibody in HCT116 and RKO after treatment with bortezomib (5 nM) or KPT330 (100 nM) for 12 h. Bars represent 10 µm. (FIG. 5B) HCT116 and RKO cells were treated with bortezomib (5 nM) or KPT330 (100 nM) for 12 h. Nuclear (N) and cytoplasmic (FIG. 5C) Extracts were separated and subjected to western blotting using p53 antibody. (FIG. 5C) HCT116 and RKO cells were treated with bortezomib (5 nM) or KPT330 (100 nM) for 12 h and subjected to western blotting using various antibodies as indicated. (FIG. 5D) The knockdown efficiency of siRNA of p53 was confirmed by real-time PCR analysis. (FIG. 5E) After knocking downing the expression of p53, HCT116 and RKO cells were treated with bortezomib (5 nM) or KPT330 (100 nM) for 72 h. Scrambled siRNA served as negative control. CCK8 assay was performed to detect cell viability in different groups. The bars represent the mean±SEM of triplicates in one experiment.

(FIG. 6A) Relative tumor growth of PDX model treated with vehicle (control), 1 mg kg/ml of bortezomib, 10 mg/kg of KPT330 or in combination measured from 0 to 21 days (n=6). (FIG. 6B) Representative H&E and IHC stained sections of PDXs and corresponding quantitative analysis. Bars represent 100 µm. The data shown represent the mean±SEM. (FIG. 6C) Relative tumor growth of 5 PDX models treated with various drugs from 0 to 31 days (n=6). The results of representative 4 drugs were shown. (FIG. 6D) The correlation between status of p53 and sensitivity of combinational treatment. (FIG. 6E) The sensitivity of all 13 drugs was shown by responsive heat map. Bars represent 100 µm. The data shown represent the mean±SEM.

(FIG. 7A) Clinical characteristics of human tumors used to generate PDXs. (FIG. 7B) A representative PDX model used in this study. (FIG. 7C) Representative H&E stained sections of the original tumors and of xenografts both at an early passage (Px1) and the passage used for the experiments (Px3). Bars represent 100 µm.

DETAILED DESCRIPTION OF THE PREFERRED EMBODIMENTS

Cell Culture

Figure 1A:
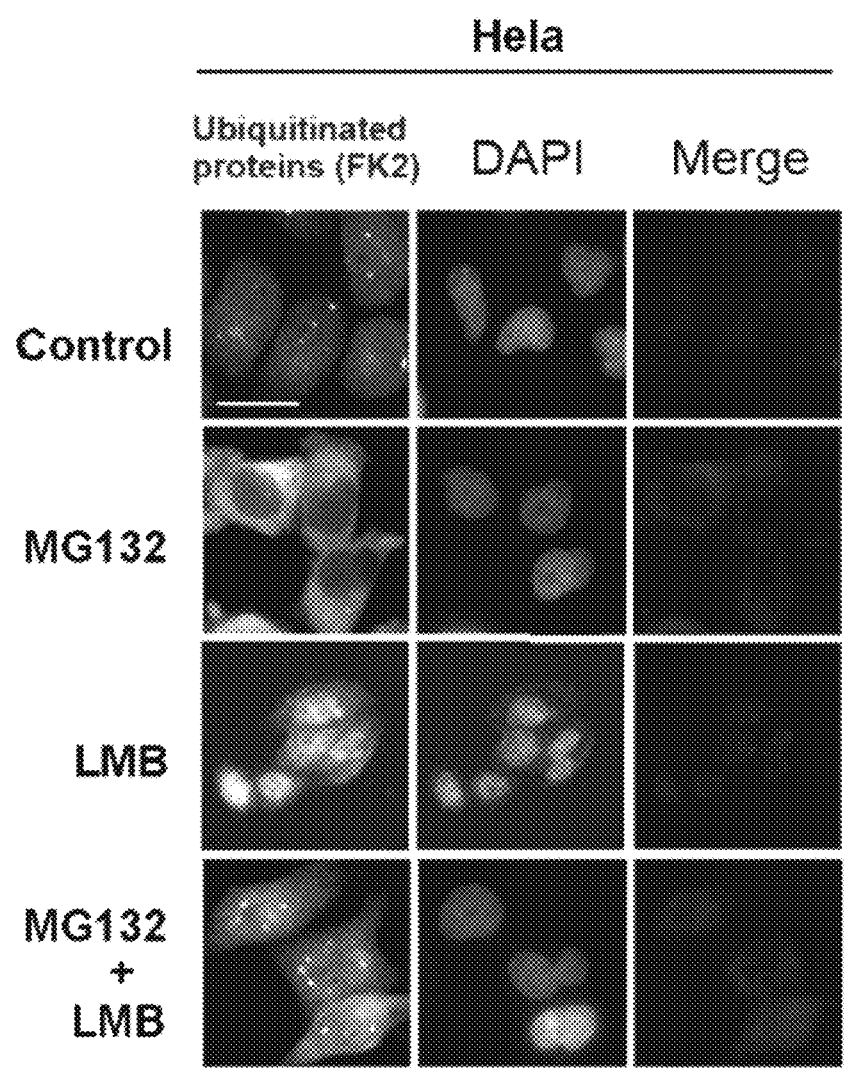
FIGS. 1A-1D show nuclear transportation of ubiquitinated proteins upon proteasome and nuclear export inhibitor treatment; wherein (FIG. 1A) HeLa cells were treated with MG132 (30 μM) and Leptomycin B (LMB, 20 nM) for 12 h as indicated. The cells were fixed and stained for ubiquitin-conjugated proteins (FK2). The nucleus was stained with DAPI.

The human cell lines Hela, SW480, SW620, HCT116 and RKO were obtained from American Type Culture Collection (ATCC), which were cultured in Dulbecco's modified Eagle's medium (DMEM; Hyclone, Logan, Utah, USA) supplemented with 10% fetal bovine serum (Hyclone, Logan, Utah, USA) and 1% penicillin/streptomycin, and were maintained at 37° C. in an incubator under an atmosphere containing 5% $CO_2$.

Cell Viability Assay

Cell viability assay were determined using the CCK8 method. Briefly, cancer cells were suspended and seeded on 96-well plates (103 cells per well) in culture medium. Twenty-four hours later, the cells were treated with the indicated drugs for an additional 72 h. 10 µL of CCK8 reagent (Dojindo, Wash., USA) was added to each well, and the plates were incubated at 37° C. for another 2 h. The absorbance was measured with a spectrophotometer at 450 nm. Two types of chemotherapeutic drugs, bortezomib (Selleck, Houston, Tex., USA) and KPT330 (Selleck, Houston, Tex., USA), were used in our study. The results of the combined treatment were analyzed according to the isobolographic method of Chou and Talalay (17) using the Calcusyn software program. The resulting combination index (CI) was used as a quantitative measure of the degree of interaction between the two drugs. CI=1 indicates additivity, CI>1 indicates antagonism, and CI<1 indicates synergism.

Immunofluorescence Staining

HCT116 and RKO cells were cultured for 24 h prior to drug treatment. Cells were then treated with 5 nM bortezomib and 100 nM KPT330 for another 24 h, then fixed with 4% paraformaldehyde. After blocking with 5% BSA for 1 h, slides were incubated overnight with anti-p53 Ab (Santa Cruz Biotechnology, Santa Cruz, Calif., USA) and anti-ubiquitinated proteins (Santa Cruz Biotechnology, Santa Cruz, Calif., USA). Cells were then washed and incubated with fluorescence conjugated goat anti-rabbit IgG for 1 h. Slides were analyzed using Leica Fluorescence Inversion Microscope System.

Western Blotting

Western blotting was performed. The following specific antibodies were used for analysis: anti-PARP, anti-Bax, anti-p21, anti-lamin A/C and anti-tublin antibodies were purchased from Cell Signaling Technology Co. (Cell Signaling Technology, Beverley, Mass., USA). Anti-actin, anti-p53, anti-ubiquitinated proteins, anti-Mdm2 and anti-Ki67 antibodies were purchased from Santa Cruz Co. (Santa Cruz Biotechnology, Santa Cruz, Calif., USA).

Apoptosis Assay

For quantification of apoptosis, the Pharmingen™ Annexin V Apoptosis Detection Kit (BD Biosciences, Rockville, Md., USA) was used according to the manufacturer's instructions. Apoptosis was further assessed by the measurement of caspase-3 and -7 activity using a luminometric Caspase-Glo-3/7 assay (Promega, Madison, Wis., USA) according to the manufacturer's protocol.

Flow Cytometric Analysis of Cell Cycle Distribution

Cells were seeded in 6-well plates and allowed to attach overnight. After treated with bortezomib (5 nM) and KPT330 (100 nM) for 48 h, cells were fixed with 75% ethanol, stained with RNase-containing PI, and analyzed by flow cytometry after 20 minutes incubation.

Mice Xenograft Studies

Nude mice (4-6 weeks old, male) were used as an in vivo mouse model. All mouse procedures were approved by the animal care and use committees of Xinhua Hospital. Mice were inoculated subcutaneously in both flanks with HCT116 cells (2*106), and these with tumors developed (~10 mm$^3$) were randomly divided into four groups. The groups were treated with vehicle (control), bortezomib (1 mg/kg, intraperitoneal administration, b.i.w.), KPT330 (10 mg/kg, oral administration, b.i.w.) or combination of bortezomib and KPT330. Tumors were measured twice a week with a caliper. Their volumes were calculated as follows: 0.5*length*width$^2$. After 18 days of treatment, the tumors were removed from euthanized mice, photographed, and paraffin imbedded.

Generation of PDXs from Colorectal Tumors

Tumor tissue specimens from freshly resected colon were washed and cut into 2- to 3-mm$^3$ pieces in antibiotic-containing PBS medium. Under anesthesia with pentobarbital, one tumor piece was implanted subcutaneously by a small incision in one side of axilla into 4-6 weeks old male nude mice. Tumors were harvested when they reached a size of 1500 mm$^3$ (Px1 xenografts). Xenografts from Px2 mice were divided into small pieces and then implanted again subcutaneously as described above to obtain Px2 xenografts. This process was further repeated and the experiments were performed on xenografts Px3.

Immunohistochemistry

Slide sections of tumor specimens were baked at 60° C. for 1 h, deparaffinized and rehydrated with xylene and ethanol. After antigen retrieval with microwave heating, endogenous peroxidase activity was blocked with 3% hydrogen peroxide. Non-specific staining was minimized by incubation in 5% FBS. Slides were then incubated with the primary antibodies at 4° C. overnight. After washed and incubated with secondary antibodies at room temperature for 1 hour, specific staining was visualized using the Horseradish Peroxidase Color Development Kit (Beyotime, Shanghai, China). Photomicrographs were taken using an Olympus microscope (Center Valley, Pa., USA). Expression index=% of positive cells×staining intensity (1+2+ or 3+).

Statistical Analysis

Statistical analyses were performed using SPSS 13.0 software. The paired, two-tailed Student's t-test was used to determine the significance between two groups. P<0.05 was regarded as the threshold value for statistical significance.

RESULTS

Proteasome Inhibitors Promote Nuclear Protein Export

Figure 1B:
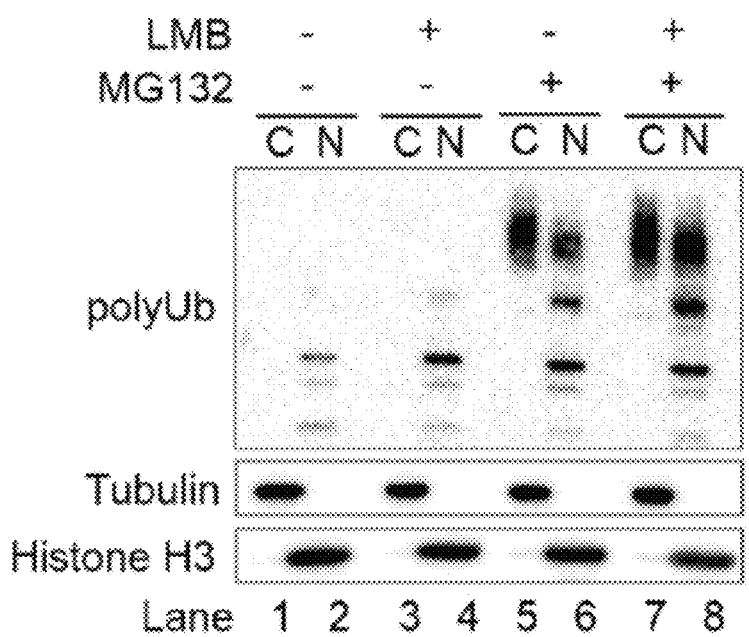
Figure 1C:
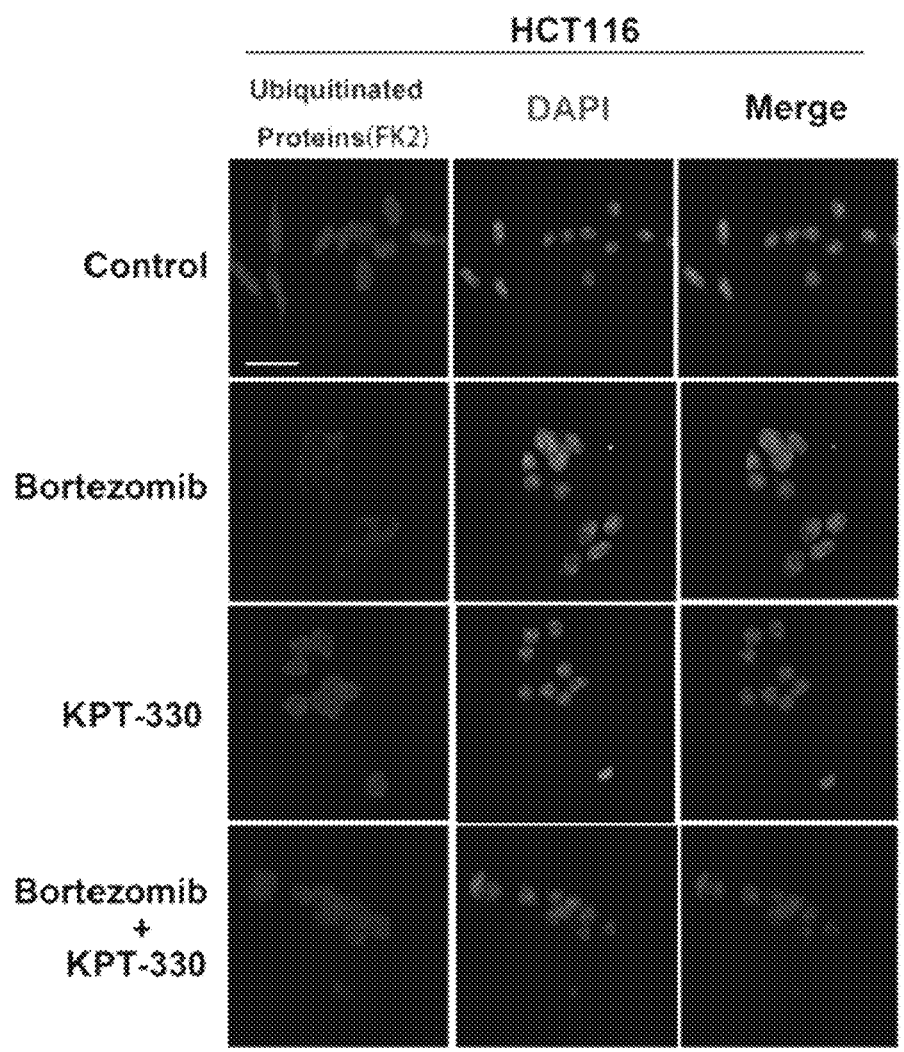
Figure 1D:
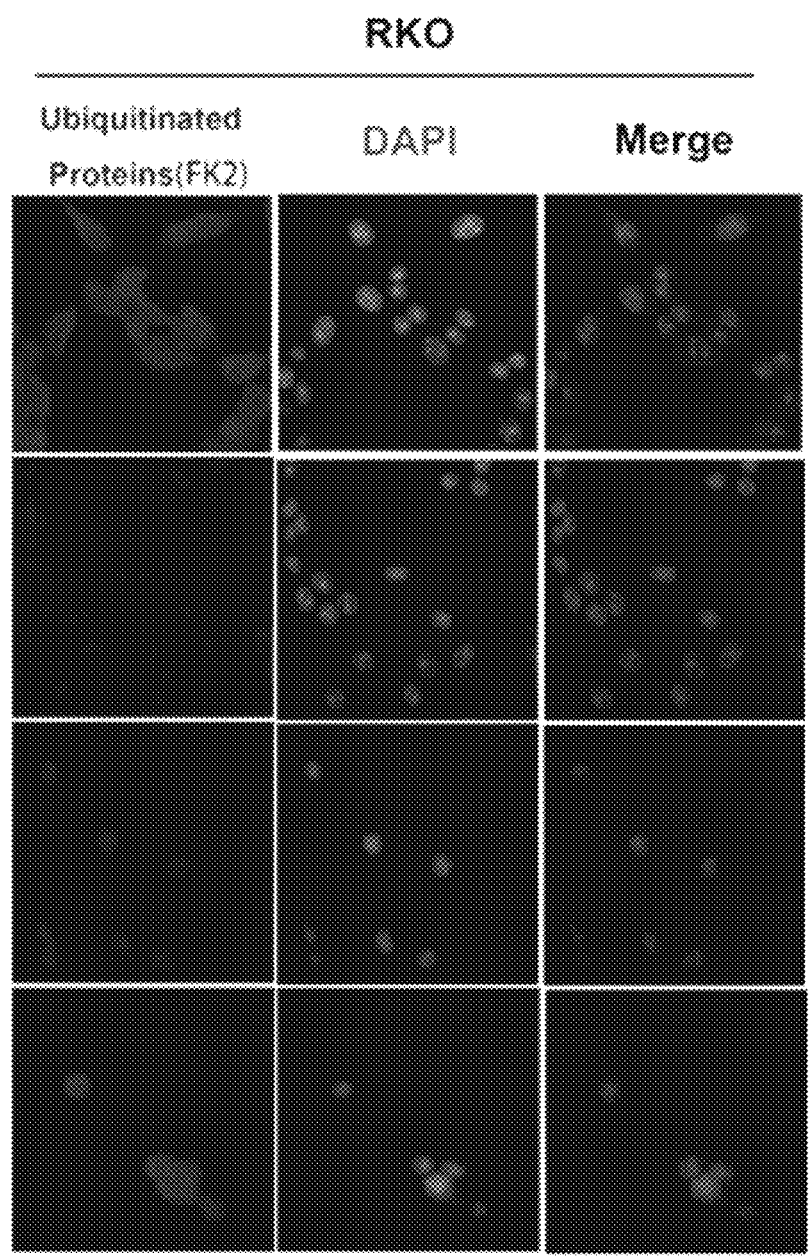

Proteasome inhibition offers an effective strategy to kill tumor cells, and proteasome inhibitors such as bortezomib have been approved to treat multiple myelomas and lymphoma. However, bortezomib or newer generation of proteasome inhibitors had minimal anti-tumor activity in patients with advanced CRC or other solid tumors. To explore the potential chemoresistant mechanisms to proteasome inhibitors, we examined the distribution of ubiquitinated proteins in proteasome inhibitor MG132-treated HeLa cells. As revealed by immunofluorescence staining, exposure to MG132 increased ubiquitinated proteins in cells, most notably in cytoplasm, whereas the predominant staining was found in the nuclei in the presence of CRM1 inhibitor LMB (FIG. 1A). Nuclear and cytosolic ubiquitinated proteins were also examined by immunoblotting after the cells were treated with the inhibitors. As shown in FIG. 1B, MG132-induced exported nuclear ubiquitinated protein increased substantially in nuclei with treatment of LMB. We then investigated the distribution of ubiquitinated protein in CRC cells HCT116 and RKO exposed to proteasome inhibitor bortezomib and CRM1 inhibitor KPT330. Similar to the finding in HeLa cells, ubiquitinated proteins were exported from nuclei upon bortezomib treatment, and combination of bortezomib and KPT330 led to increased ubiquitinated protein in the nuclei (FIGS. 1C and D). These results indicated that proteasome inhibition promotes the export of ubiquitinated protein ubiquitinated protein from nuclei. It is likely that the nuclear exportat signals (NESs) in these proteins are responsible for proteasome inhibition-induced nuclear export.

Inhibition of Nuclear Export Enhances the Cytotoxic Effects of Bortezomib

Figure 2A:
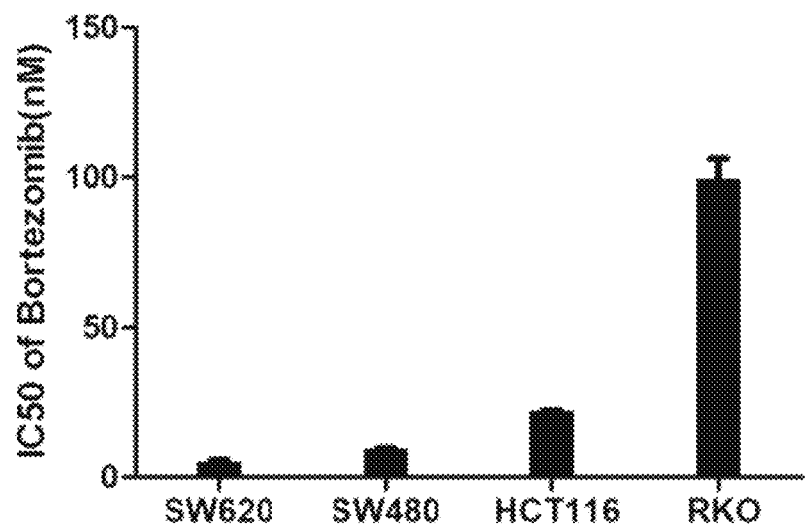
Figure 2A:
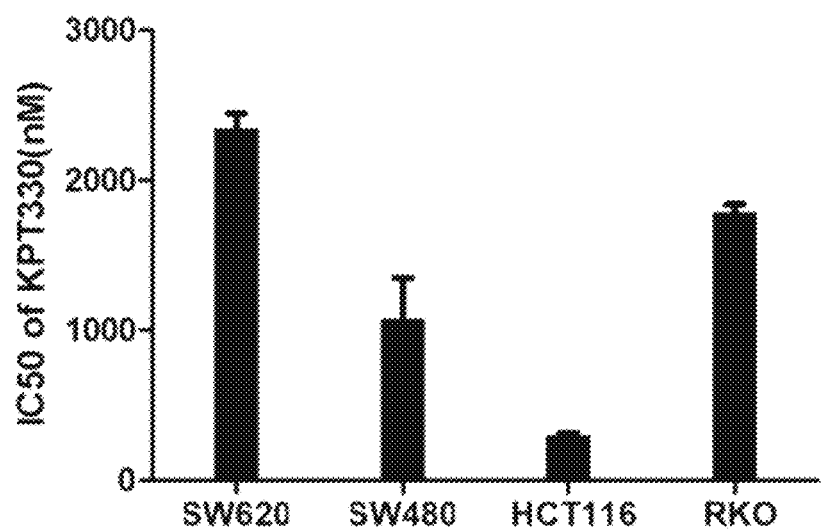
Figure 2B:
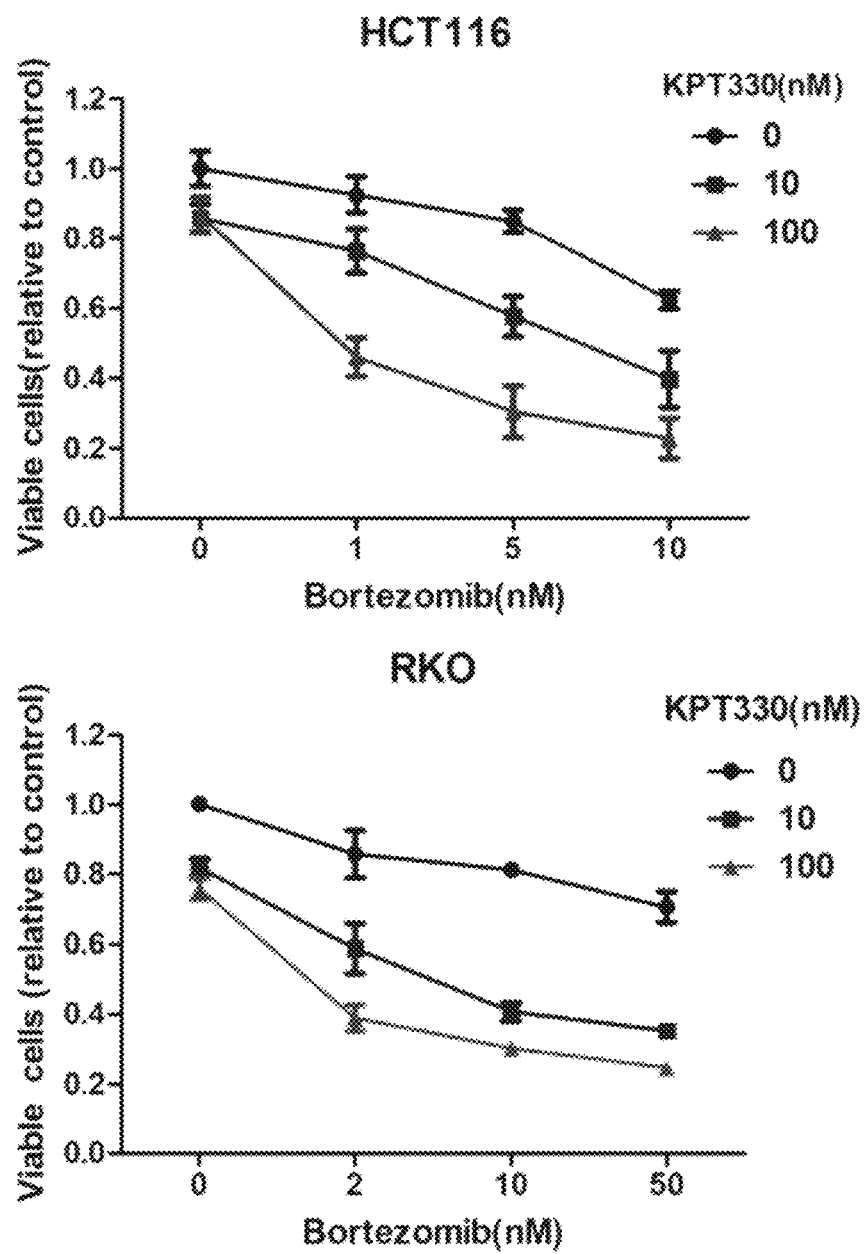
Figure 2C:
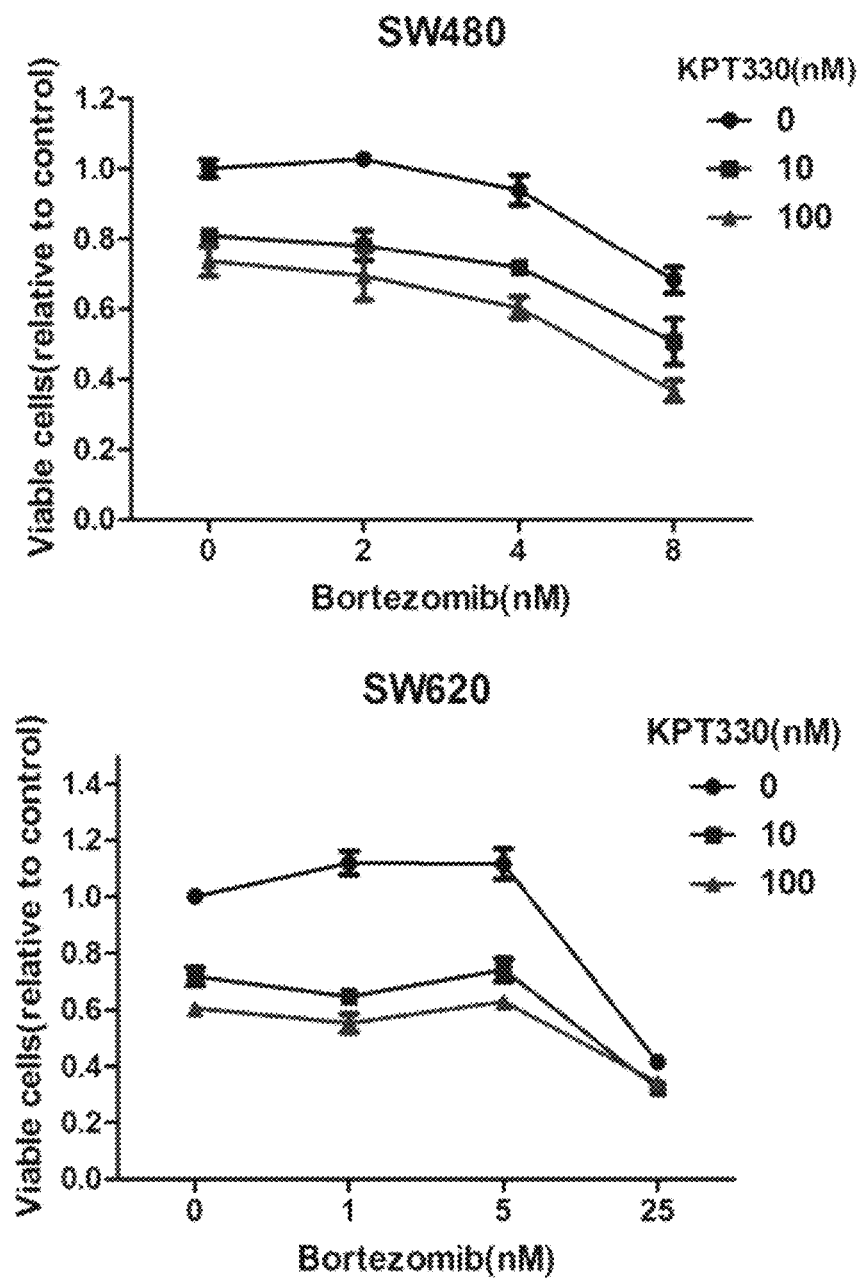

To assess whether the export of nuclear proteins is related to the cytotoxic action of bortezomib, colorectal cancer cells HCT116, RKO, SW480 and SW620 cells were cultured in the presence of different concentrations of bortezomib or KPT330 for 72 h. The IC50 of different cells indicated that HCT116 and RKO were moderately more resistant to bortezomib compared with SW480 and SW620 (22 and 99 nM vs. 5 and 9 nM) (FIG. 2A), whereas all of them were relatively insensitive to KPT330 (303, 1790, 1079, and 2345 nM respectively) (FIG. 2A). When indicated amounts of bortezomib were combined with KPT330, a markedly greater inhibition of proliferation was observed in all the cells (FIGS. 2B and C). Noteworthily, CI (Combination Index) value from isobologram analysis (17) revealed that there is a synergistic effects between bortezomib and KPT330 in HCT116 (p53 wild type) and RKO (p53 wild type) cells with CI<1 (FIG. 2D), but not in SW480 (p53 mutant) and SW620 (p53 mutant) cells. Under microscope, there were also profound morphological alterations when the cells were exposed to bortezomib in the presence of KPT330 (FIG. 2E). Furthermore, combination of bortezomib and KPT330 had significantly increased inhibition on colony formation on HCT116 cells than either drug alone (FIG. 2F). These results suggest that the synergistic effects depend on the function of p53.

Figure 2G:
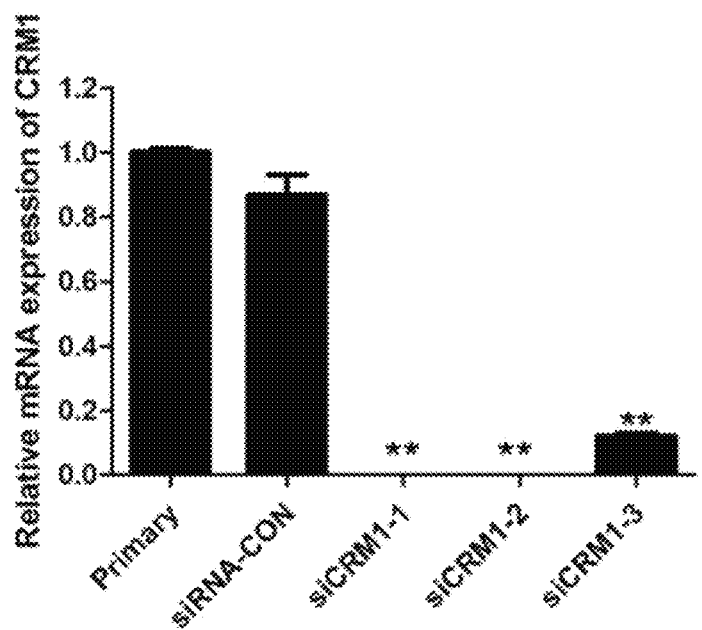
Figure 2H:
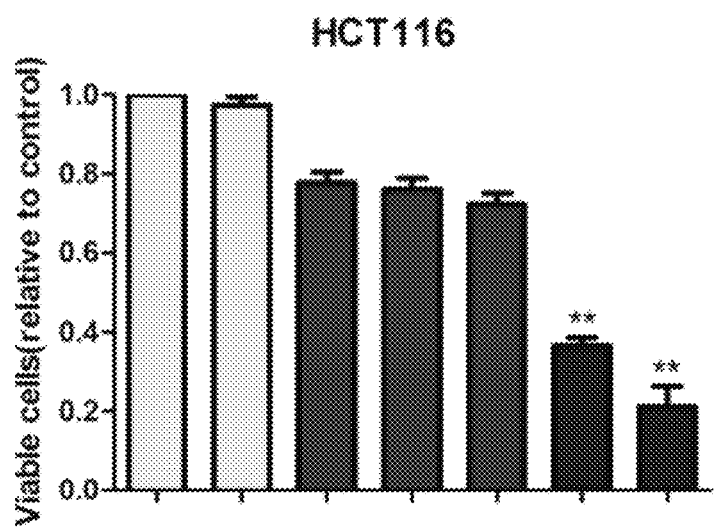

To minimize the possibility that the effect of KPT330 is a result of its action on cellular processes other than nuclear exportation, we knocked down CRM1 in HCT116 cells using 2 specific siRNAs. The efficiency of specific siRNA on CRM1 level was confirmed by real-time PCR analysis (FIG. 2G). As shown in FIG. 2H, similar to KPT330 treatment, CRM1 knockdown significantly enhanced the cytotoxic effect of bortezomib. Taken together, these results demonstrated that inhibition of nuclear exportation synergistically enhanced the cell killing activity of proteasome inhibition in p53+/+ colon cancer cells HCT116 and RKO.

Bortezomib and KPT330 Induce Apoptosis and Cell Cycle Arrest in Sensitive Cells

Figure 3A:
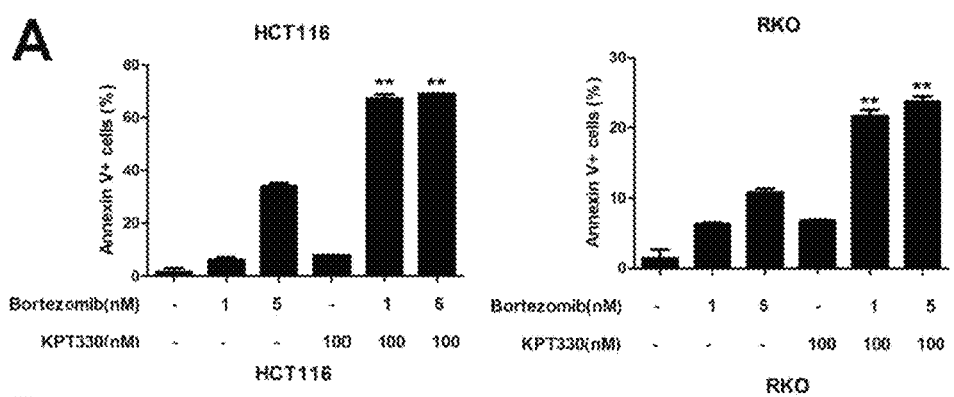
FIGS. 3A-3F show bortezomib and KPT330 enhance apoptosis in HCT116 and RKO cells.
Figure 3B:
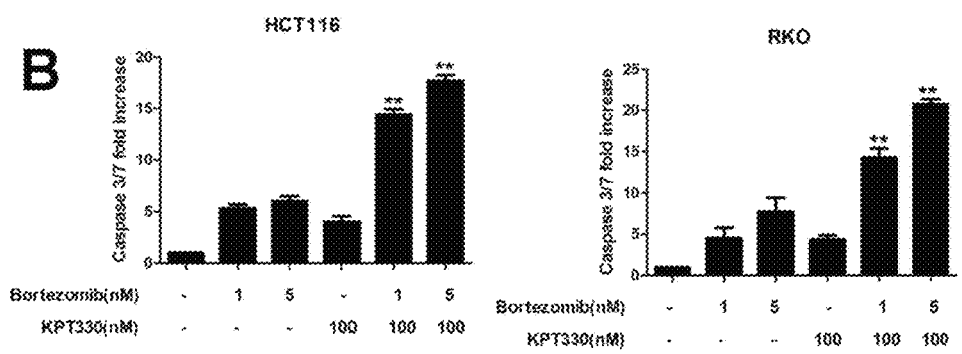
Figure 3C:
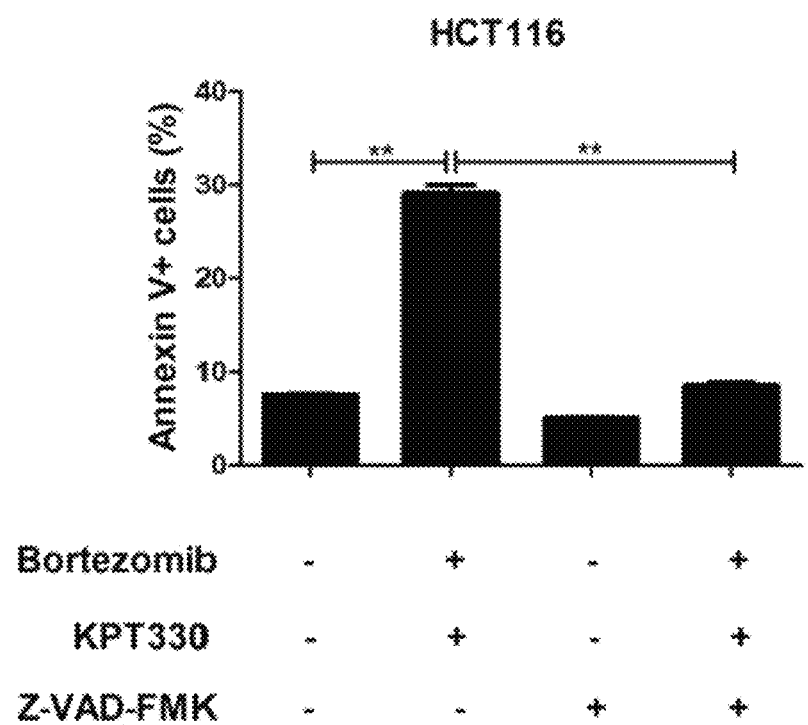
Figure 3D:
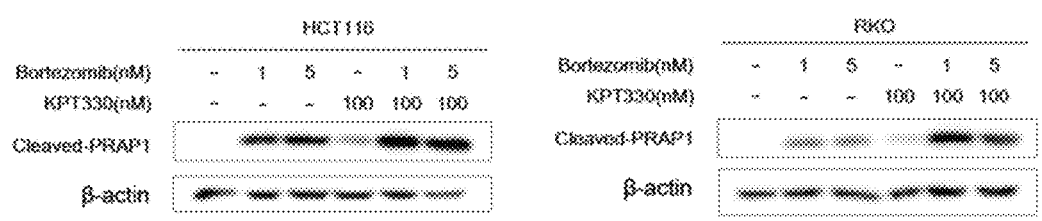
Figure 3E:
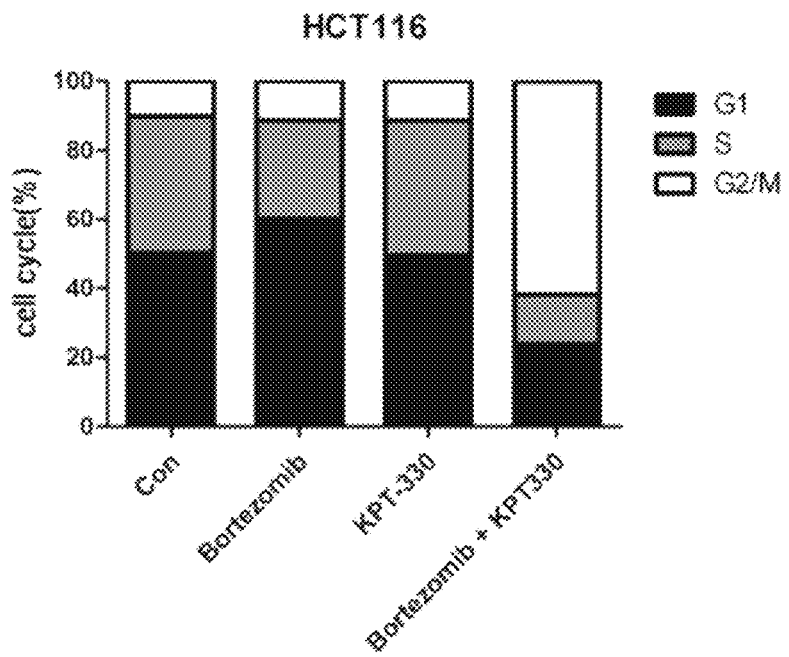
Figure 3F:
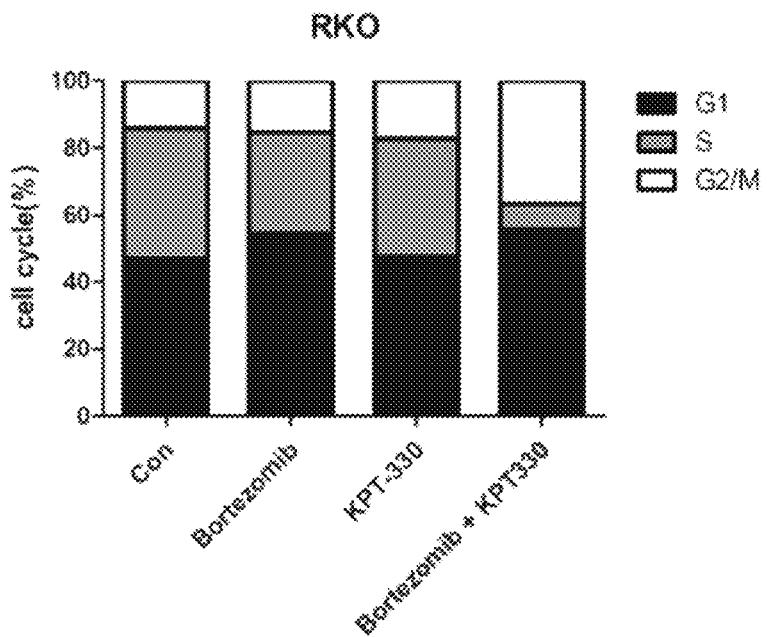

To further understand the cytotoxic effects of bortezomib and KPT330 on HCT116 and RKO cells, annexin V staining and caspase 3/7 activities were assessed using the flow cytometric analysis and luminometric Caspase-Glo-3/7 assay kit. While the relative low doses of each drug alone induced a moderate increase of annexin V staining and caspase 3/7 activation, their combination markedly augmented both the staining and the activation (FIGS. 3A and B). The increased annexin V staining was effectively inhibited by the caspase inhibitor Z-VAD-FMK (FIG. 3C). Moreover, The combination of bortezomib and KPT330 also led to more PARP1 cleavage in HCT116 and RKO cells, indicating synergetic apoptotic effect of the two agents (FIG. 3D). The effects of bortezomib and KPT330 on cell cycle were further examined. While the compounds alone did not significantly change cell cycles, HCT116 and RKO cells exposed to both bortezomib and KPT330 underwent a G2/M cell cycle arrest (FIGS. 3E and F), which is a hallmark of p53-mediated cell cycle block (18).

Figure 4A:
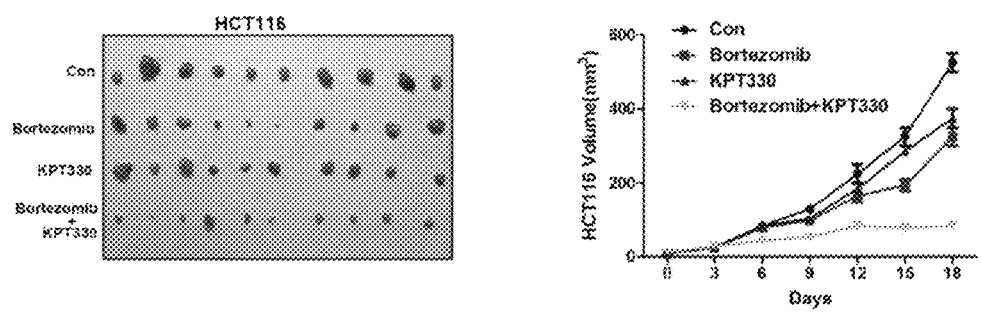
FIGS. 4A-4C show bortezomib and KPT330 co-treatment inhibit HCT116 xenografts in nude mice.
Figure 4B:
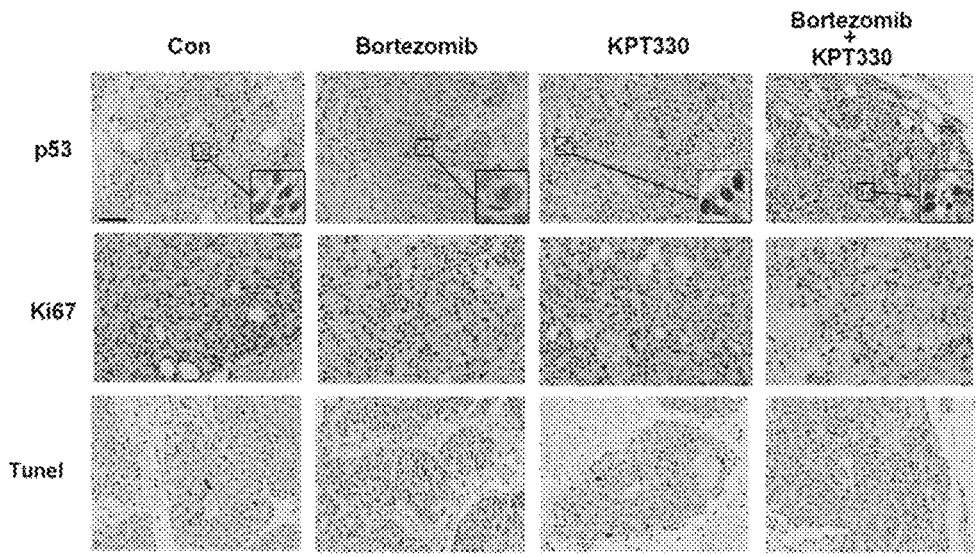
Figure 4C:
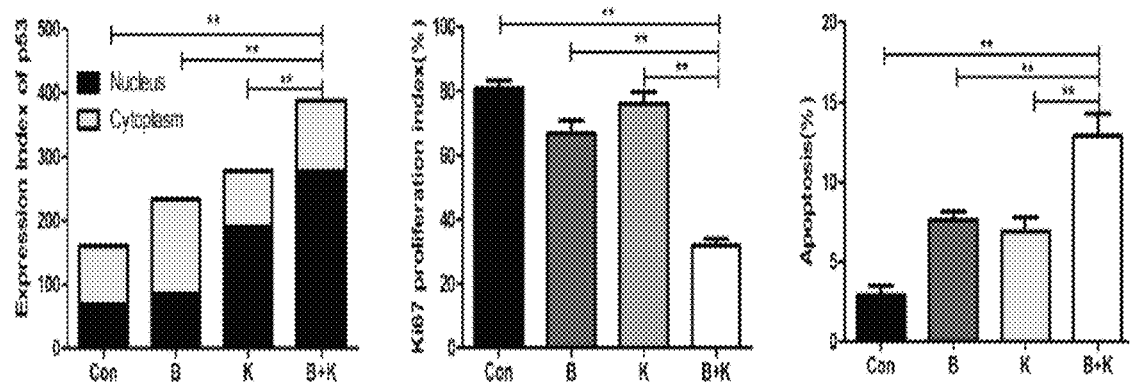

These findings prompted us to examine the action of KPT330 and bortezomib on tumor xenografts derived from HCT116 cells in nude mice. The tumor-bearing nude mice were randomly assigned to receive vehicle, bortezomib, KPT330 or both. They showed tolerance to treatment and maintained normal activities. Regular twice a week measurements found no marked changes in body weight (data not shown). After 18 days of treatment, the mice were euthanized to dissect the tumors. The combination of the drugs significantly enhanced tumor growth inhibition compared with vehicle (83.8% tumor reduction, P<0.001), bortezomib (45.7% tumor reduction, P<0.001), or KPT330 (55.2% tumor reduction, P<0.001) by the final day of treatment (FIG. 4A). The expression of p53, Ki67 and DNA fragmentation in the tumors were then evaluated by IHC and Tunel assay (FIG. 4B). Compared with these from vehicle group, bortezomib treatment decreased the ratio of nuclear/cytoplasmic p53 in the tumor (0.57 vs 0.73, p<0.001), whereas KPT330 and bortezomib combination significantly increased the ratio (2.52 vs 0.73, p<0.001) compared with control group (FIG. 4C). Interestingly, similar to the finding in cell culture, the combination of bortezomib and KPT330 also significantly increased the level of p53 in tumors. Furthermore, compared with vehicle or either drug alone, the combination treatment resulted in significantly reduced level of Ki67 and increased DNA fragmentation, indicating that these tumors had the decreased cell growth and likely p53-mediated apoptosis (FIG. 4C).

Nuclear p53 Plays a Critical Role in Synergistic Cytotoxic Effect

Figure 5A:
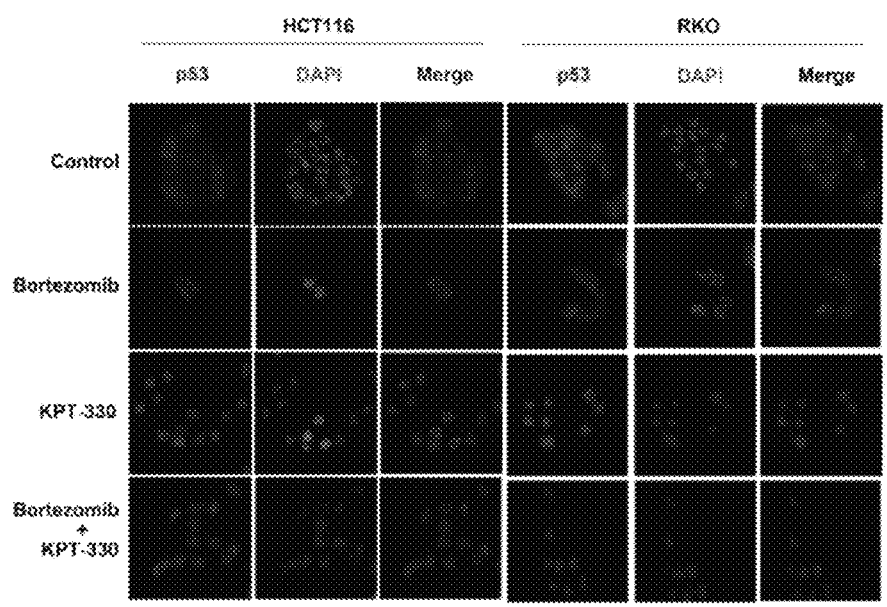
FIGS. 5A-5E show nuclear p53 plays a critical role in synergistic cytotoxic effect.
Figure 5B:
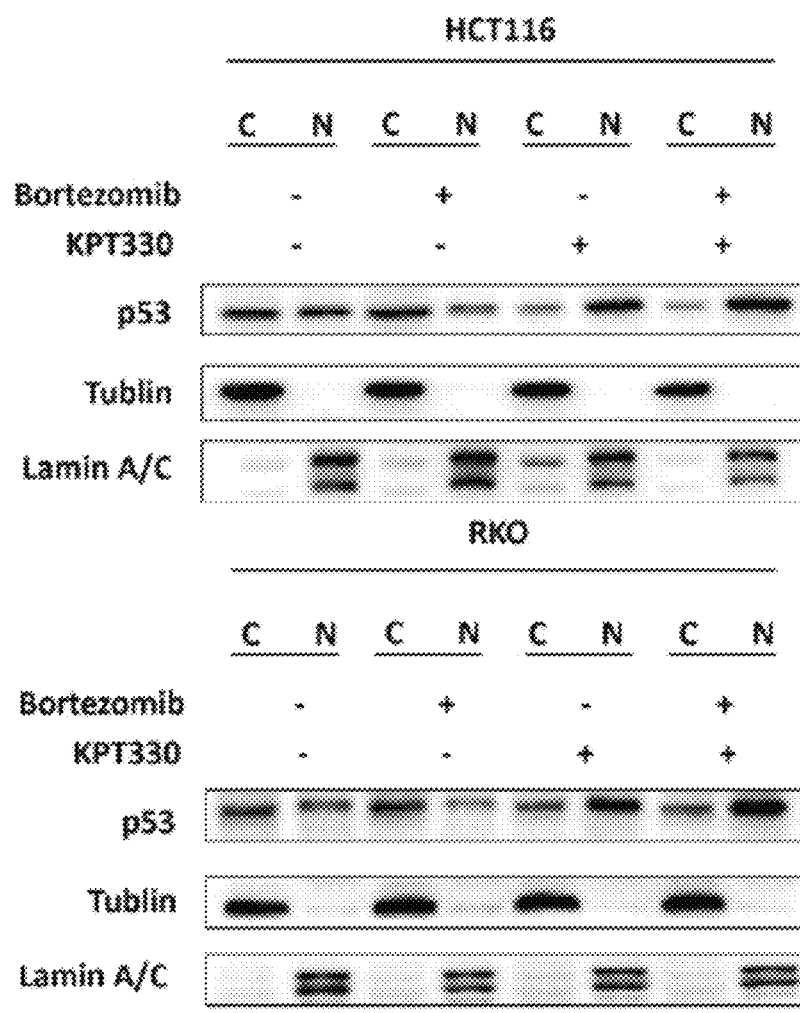

The level of p53 in cells is mainly controlled through ubiquitination and proteasomal degradation. Association of p53 expression with the cytotoxic effect of KPT330 and bortezomib prompted us to examine its sub-cellular localization. In HCT116 and RKO cells, accumulated p53 upon bortezomib treatment was mostly in cytoplasm, whereas co-treatment with KPT330 resulted in a predominant nuclear staining of p53 (FIG. 5A). To further confirm the result, cellular fractionation was performed to examine p53 in nuclei and cytosol by immunoblotting. As shown in FIG. 5B, the results were consistent with the findings from immunofluorescence and indicated that bortezomib induced the nuclear export of p53 was in both HCT116 and RKO cells, whereas it could be effectively blocked by KPT330.

Figure 5C:
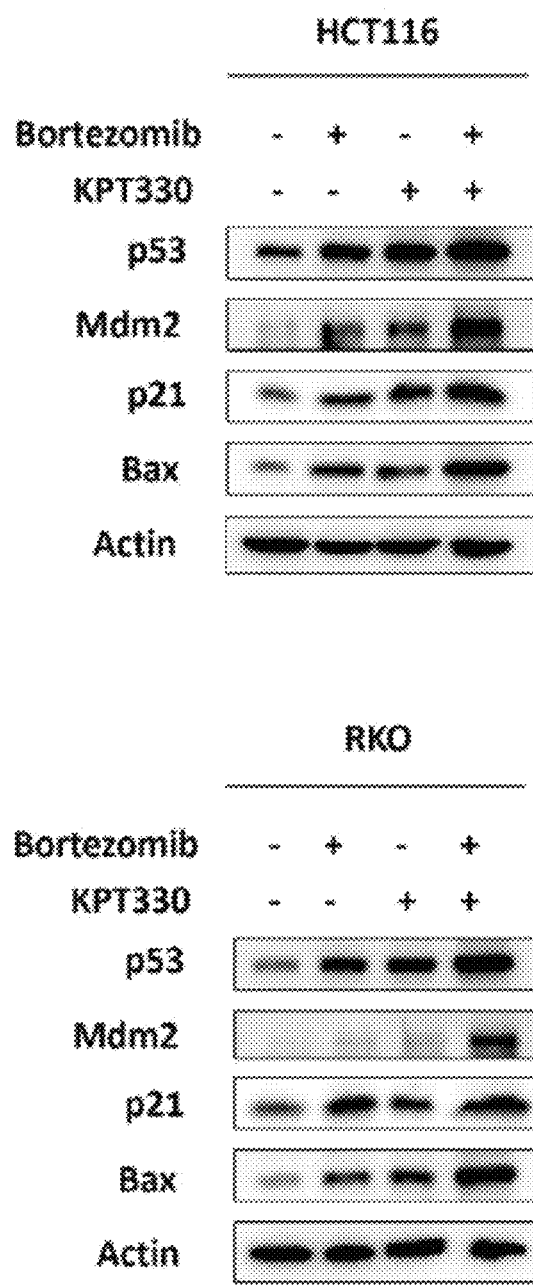
Figure 5D:
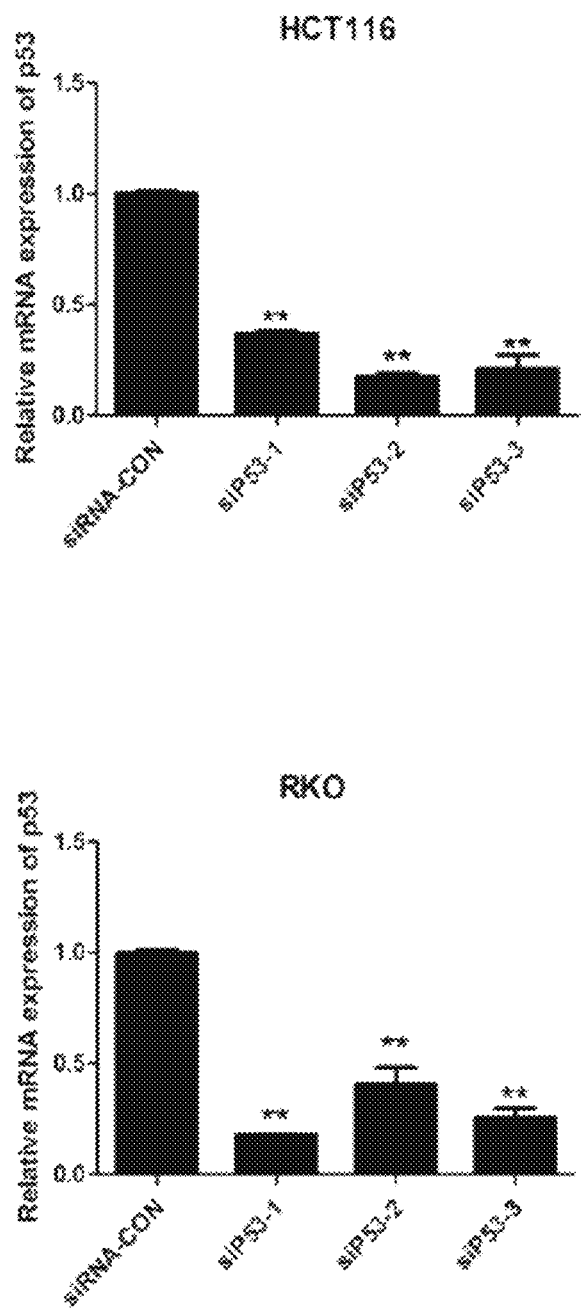
Figure 5E:
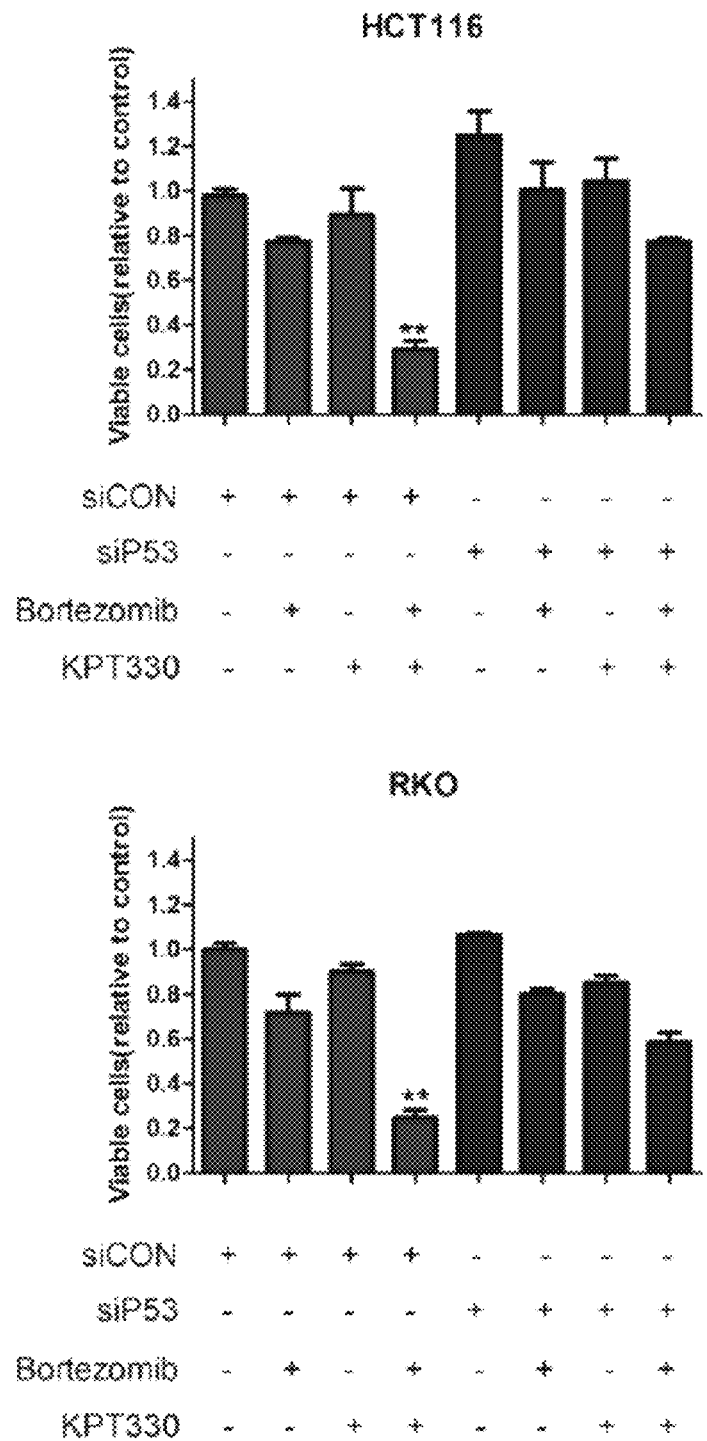
Figure 6A:
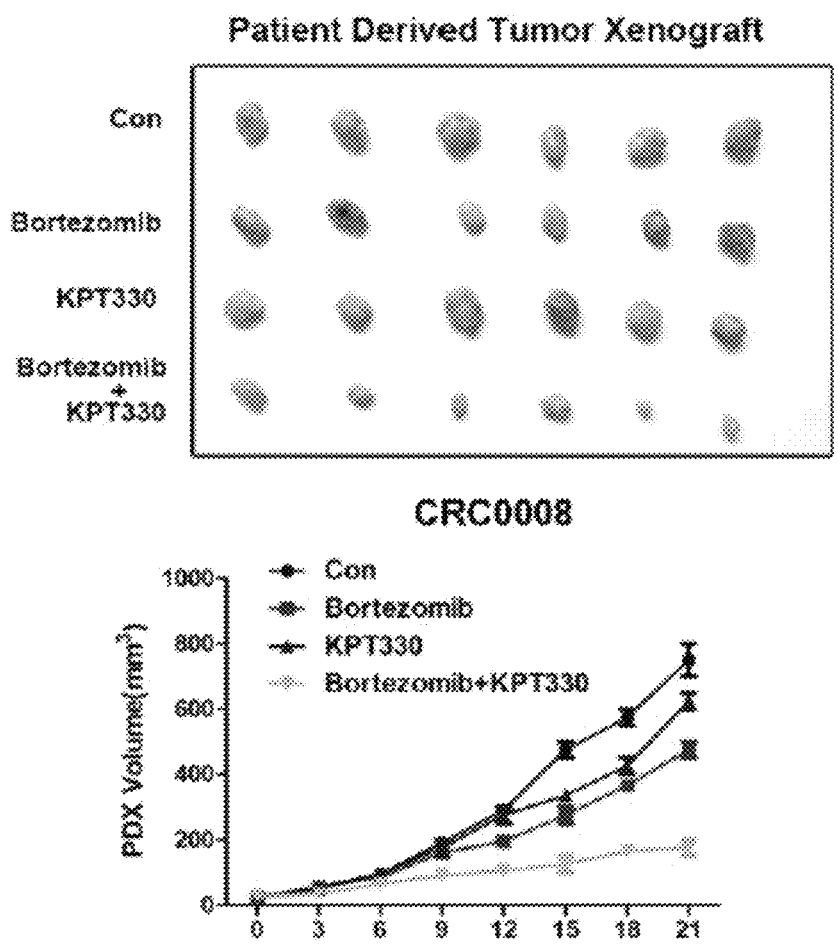
FIGS. 6A-6E show bortezomib and KPT330 co-treatment inhibit patients-derived xenografts in nude mice.
Figure 6B:
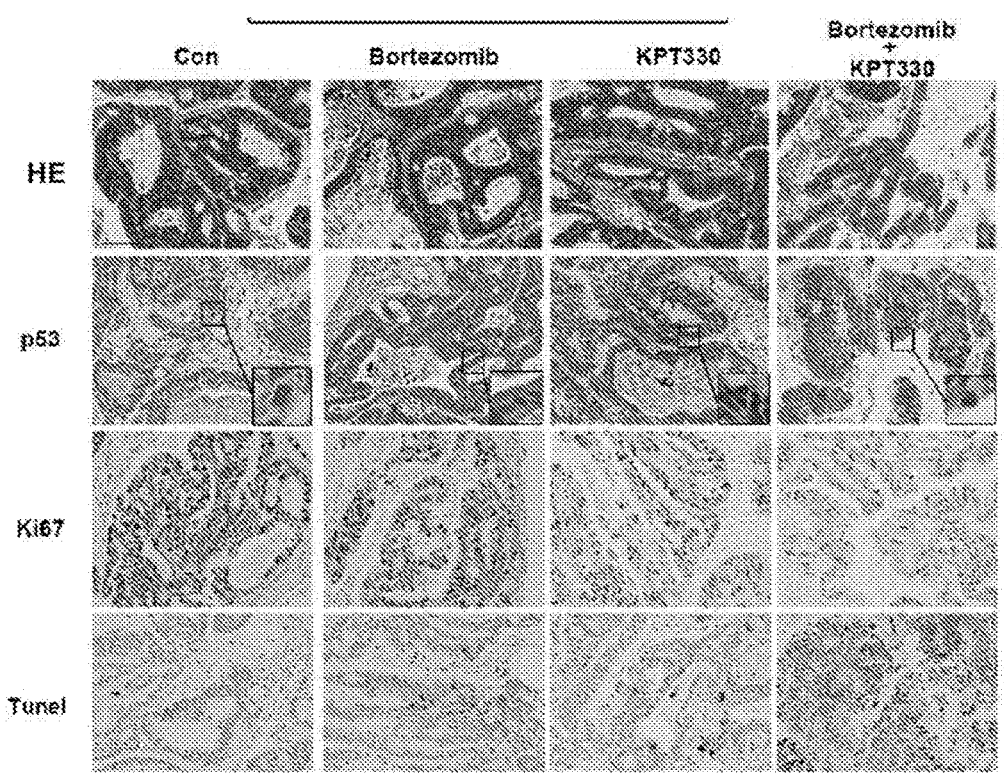
Figure 6B:
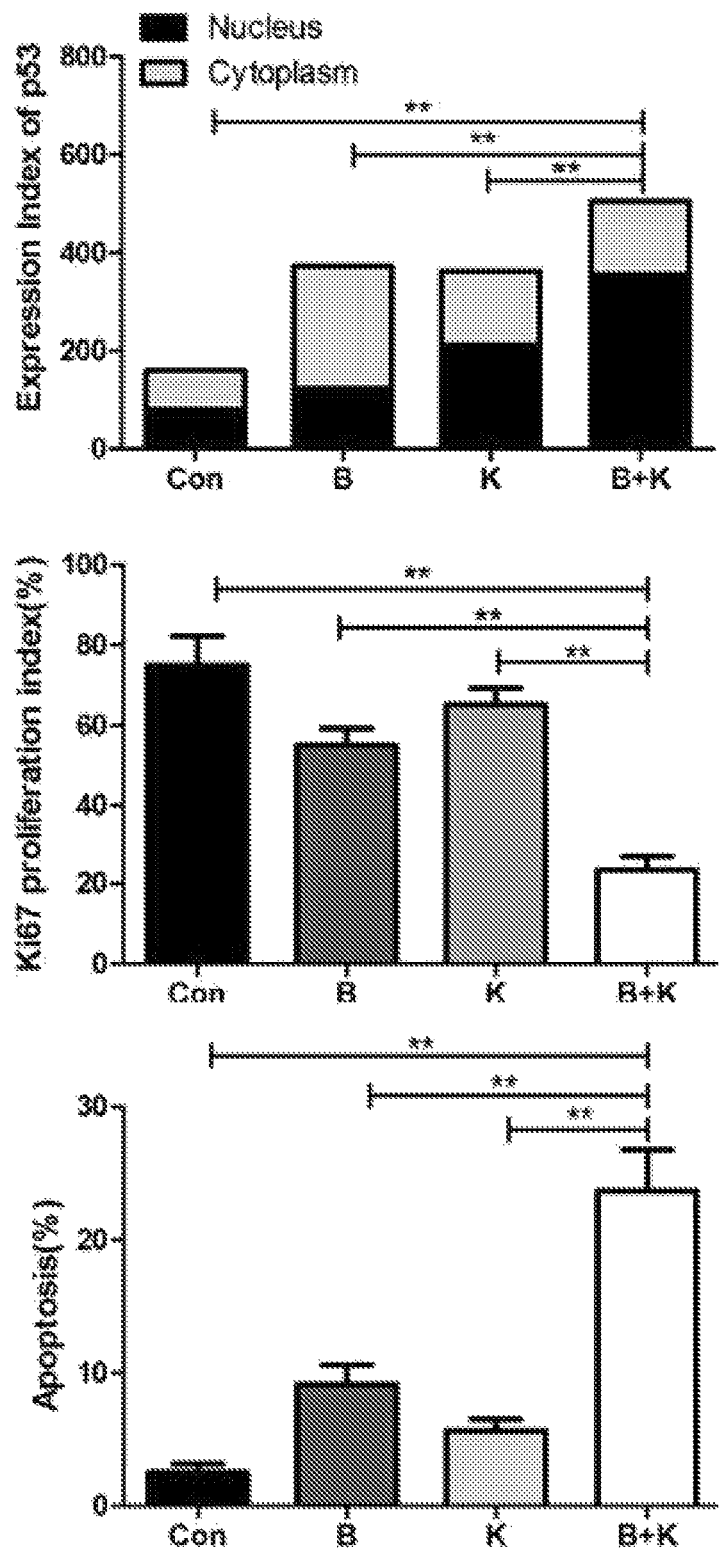
Figures 7A, 7B:
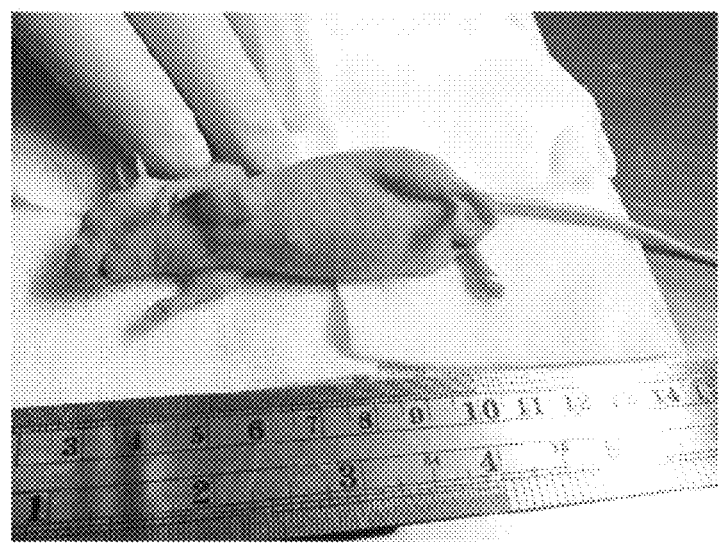
FIGS. 7A-7C show characteristics of human colorectal tumors used for xenografts.
Figure 7C:
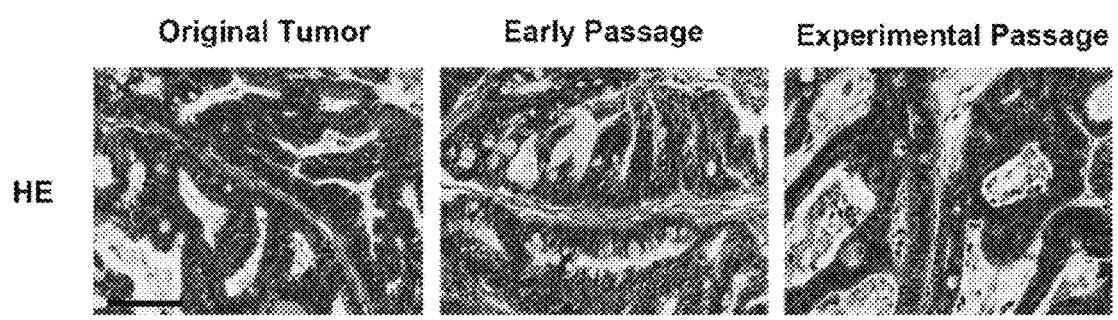

It is conceivable that nuclear retention of p53 might reduce its preoteasomal degradation and activate the transcription of its target genes. We therefore analysed the level of p53 and the expression of its targeted genes p21, Bax, and Mdm2. As shown in FIG. 5C, KPT330 further increased bortezomib-induced p53 accumulation, and the expression of Mdm2, p21, and Bax. These changes likely account for the synergistic apoptosis and G2/M arrest when HCT116 and RKO cells were treated with bortezomib and KPT330. To further determine the pivotal role of p53 in the process, we used siRNA to knock down its expression, which was confirmed by real-time PCR analysis (FIG. 5D). As shown in FIG. 5E, the synergistic cytotoxic effect of bortezomib and KPT330 was markedly attenuated by p53 knockdown. It is not clear at this moment whether the lack of complete reverse is duo to experimental limitations or involvement of additional factors in the synergistic Patients-Derived Xenografts Contained Functional p53 Were Sensitive to Bortezomib and KPT330 Treatment To further evaluate the potential therapeutic effects of bortezomib and KPT330, patient-derived primary human CRC xenografts (PDX model) were established and used in our study. We were able to transplant tumor tissues from a patient with stage III rectal cancer (p53+/+) into nude mice (FIG. 7A). After the initial xenografts were established, they were re-implanted into a panel of nude mice to expand the colony (FIG. 7B). Examining H&E-stained tumor sections indicated that the initial xenografts and their passages were histologically similar to the original tumors (FIG. 7C). We then monitored the growth of these PDXs after various treatments. Compared with tumors from the control group, bortezomib or KPT330 alone led to mildly tumor regression (36.6% and 16.7% reduction respectively), whereas their combination inhibited tumor growth significantly more effective (76.7% tumor reduction, P<0.001) (FIG. 6A). Similar to the findings in HCT116 xenograft, the ratio of nuclear/cytoplasmic p53 protein was decreased in bortezomib group compared with the control group (0.49 vs 0.98, p<0.001), whereas combination of bortezomib and KPT330 treatment increased the ratio significantly (2.36 vs 0.98, p<0.001). Furthermore, the combination treatment markedly reduced Ki67 expression detected by IHC, and increased apoptosis detected by H&E staining and the Tunel assay (FIG. 6B).

Figure 6C:
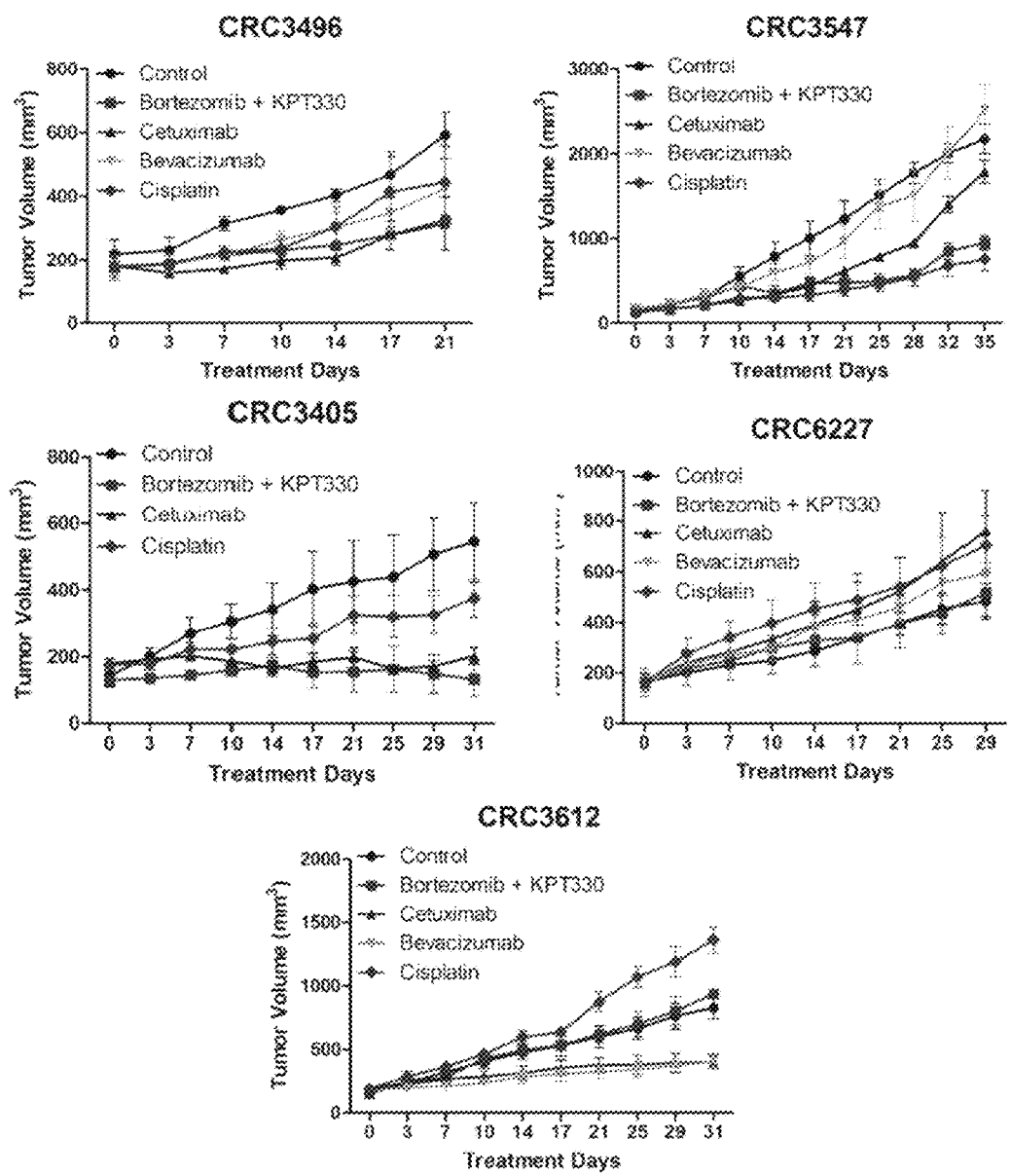
Figures 6D, 6E:
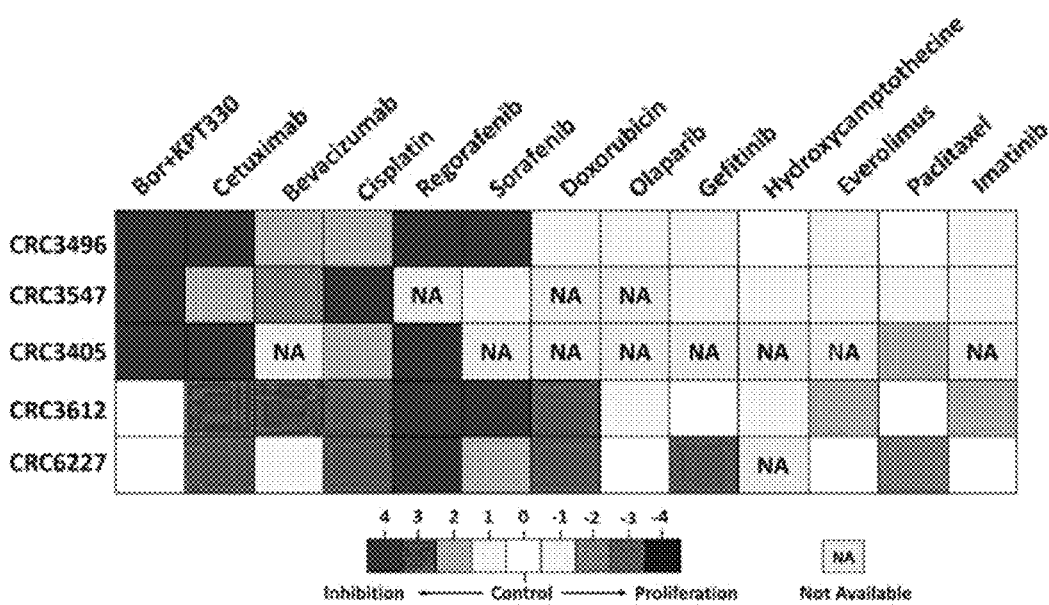

To further assess the efficacy of bortezomib and KPT330 combination treatment, additional primary tumor-derived xenografts from 5 CRC patients, who were all resistant to conventional FOLFOX regimen (5-Fluorouracil; Oxaliplatin) and underwent relapse within one year after surgery, were tested (FIG. 7A). As shown in FIG. 6C, 3 of the xenografts were sensitive to bortezomib and KPT330 treatment, and 2 were relatively not sensitive. Among the sensitive xenografts, CRC3496 and CRC3547 contained wild type p53, whereas CRC3405 harbored the C176Y p53 mutation. Interestingly, it has been shown that p53 with C176Y mutation was transcriptional active in a number of experimental systems (19). Thus, xenografts that are sensitive all possess a functional p53. For the 2 xenografts that are insensitive to the combination treatment, CRC6227 had the loss-of-function p53 mutation (G245V) (19-21), and CRC3612 contained a wild type p53 (FIG. 6D).

For the purpose of comparison, these PDXs were also treated with various therapeutics, including Cetuximab, Bevacizumab, Cisplatin, Regorafenib, Sorafenib, Doxorubicin, Olaparib, Gefitinib, Everolimus, Everolimus, and Imatinib. The representative results of 4 drugs on tumor growth were plotted with that of bortezomib and KPT330 (FIG. 6C) and the responsive heat map of all 13 drugs was produced (FIG. 6E). In the PDXs that are sensitive to bortezomib and KPT330, the combination was the most effective therapeutics. Noteworthily, the two PDX not sensitive to the combination treatment (CRC6227 and CRC3612) were also resistant to cisplatin and doxorubicin, two drugs that act on DNA and are known to induce p53 activation (22, 23). Thus, it is conceivable that the tumor CRC3612 has defect in response to p53. Taken together, these findings provide a rational basis for the clinical use of this combination for the treatment of CRC patients with wild type p53.

Discussion

Despite extensive investigations and clinical trials, development of resistance to chemotherapy remains a major challenge for the treatment of CRC (24). In the effort to explore the mechanisms of the resistance and find novel strategies and targets to improve the prognosis of CRC patients, we found that proteasome inhibition induced export of ubiquitinated nuclear proteins in CRC cells, which might represent a mechanism of chemoresistance. It has been found that CRM1, the transport protein responsible for nuclear export of many major tumor suppressors and growth regulators, is up-regulated in many tumors (25). Small molecules targeting CRM1 have been developed, and FDA has designated one of the inhibitor Selinexor (KPT330) orphan drug status for certain types of leukemia and lymphoma (15, 16). We demonstrated in this study that inhibition of nuclear export sensitized CRC cells to the cytotoxic action of proteasome inhibitor, which led to G2/M cell cycle block and apoptosis.

Tumor suppressor p53 functions as a critical guardian of genome. In response to genotoxic stimuli, upregulated p53 induced G2/M cell cycle arrest and apoptosis (26, 27). As cellular level of p53 is mainly controlled through ubiquitination-mediated proteasomal degradation, proteasome inhibitors are known to accumulate p53 in cells (28, 29). We found in the study that proteasome inhibition induced nuclear export of p53, and bortezomib and KPT330 have synergistic cytotoxic action on CRC cell lines with wild type p53 in vitro and in nude mice, but not the cells with mutated p53. In the sensitive cells, the combination treatment led to further increased nuclear p53 and expression of target genes. Furthermore, knockdown of p53 largely abolished the synergistic action. These results indicated that KPT330 and bortezomib together increases nuclear p53, which in turn initiates the apoptosis program in tumor cells. It is worth noting that both proteasome and CRM1 inhibitors have profound effects on many cellular processes and may kill tumor cells through a variety of mechanisms. In our study, bortezomib and KPT330 can effectively kill CRC cells containing mutated p53 (SW480 and SW620). However, their cytotoxic actions are not synergistic in these cells, suggesting the two drugs induced cell death though different pathways in these cells.

While tumor cell line-derived xenografts have been used for decades in assessing cytotoxic action against tumor cells, they are limited in many aspects to mimic human tumors, including reduced intra-tumoral heterogeneity, lack of stromal cells and modest diversity of molecular subtypes (30). Patient-derived xenografts in mice, which largely avoided these limitations and provided a more accurate depictions of human tumors, have become a "gold standard" for evaluating anti-tumor chemotherapeutics (30, 31). It has been shown that the effect of drugs on PDXs from colorectal tumors correlated with clinical outcome (31). We generated primary tumor derived xenografts from 6 patients who were chemoresistant to conventional FOLFOX regimen and had early relapsed CRC. The data indicated that the combination of bortezomib and KPT330 was more effective than either drug alone or other therapeutics in inhibiting tumor growth, and the 4 PDXs that response to the combination therapy all contained functional p53, supporting its further clinical trial. Noteworthily, we also tested a number of therapeutics on these PDXs. The two PDXs that did not response to bortezomib and KPT330 also failed to be inhibited by the treatment of cisplatin and doxorubicin, 2 drugs that act on DNA and induce p53 (22, 23). It is conceivable that these 2 tumors have defects in p53 signaling pathway.

In summary, our preclinical data suggest that CRC cells could exert self-protective function upon proteasome inhibition through nuclear export of ubiquitinated proteins, including p53. CRM1 inhibitor KPT330 synergistically sensitizes CRC cells to bortezomib treatment in vitro and in vivo, through inhibiting nuclear export and restoring functions of p53. Taken together, these findings provide a rational basis for the clinical use of this combination for the treatment of CRC patients with wild type p53.

What is claimed is:

1. A pharmaceutical composition for treating colorectal cancer, comprising
   a proteasome inhibitor or a pharmaceutically acceptable salt, solvate, hydrate, cocrystal or prodrug thereof; and
   a nuclear export inhibitor or a pharmaceutically acceptable salt, solvate, hydrate, cocrystal or prodrug thereof,
   wherein the proteasome inhibitor is bortezomib; and
   wherein the nuclear export inhibitor is KPT 330.

2. The pharmaceutical composition as claimed in claim 1, wherein the pharmaceutical composition has synergistic effects on inducing apoptosis of colorectal cancer cells.

3. A method for treating colorectal cancer, comprising administrating to a subject in need thereof a pharmaceutical composition comprising a proteasome inhibitor or a pharmaceutically acceptable salt, solvate, hydrate, cocrystal or prodrug thereof, and a nuclear export inhibitor or a pharmaceutically acceptable salt, solvate, hydrate, cocrystal or prodrug thereof, as an active agent,
   wherein the proteasome inhibitor is bortezomib; and
   wherein the nuclear export inhibitor is KPT 330.

4. The method as claimed in claim 3, wherein the subject has colorectal cancer cells containing wild type p53.

5. The method as claimed in claim 3, wherein the pharmaceutical composition is administrated to the subject intramuscularly, orally or intravenously to result in an effective dosing regimen.

6. The method as claimed in claim 3, wherein the pharmaceutical composition is administered to the subject at least three times a week.

7. A method for treating colorectal cancer, comprising simultaneously administering to a subject with a proteasome inhibitor and a nuclear export inhibitor,
   wherein the proteasome inhibitor is bortezomib; and
   wherein the nuclear export inhibitor is KPT 330.

8. The method as claimed in claim 7, wherein the subject has colorectal cancer cells containing wild type p53.

9. The method as claimed in claim 7, wherein the proteasome inhibitor and the nuclear export inhibitor are administered to the subject intramuscularly, orally or intravenously.

10. The method as claimed in claim 7, wherein the proteasome inhibitor and the nuclear export inhibitor are administered to the subject at least three times a week.

* * * * *